US 6,750,005 B2

(12) United States Patent
Leif et al.

(10) Patent No.: US 6,750,005 B2
(45) Date of Patent: Jun. 15, 2004

(54) REAGENT SYSTEM AND METHOD FOR INCREASING THE LUMINESCENCE OF LANTHANIDE(III) MACROCYCLIC COMPLEXES

(76) Inventors: Robert C. Leif, 5648 Toyon Rd., San Diego, CA (US) 92115-1022; Lidia Vallarino, 1009 West Ave., Richmond, VA (US) 23220

( * ) Notice: Subject to any disclaimer, the term of this patent is extended or adjusted under 35 U.S.C. 154(b) by 242 days.

(21) Appl. No.: 10/010,597

(22) Filed: Dec. 6, 2001

(65) Prior Publication Data

US 2002/0132992 A1 Sep. 19, 2002

Related U.S. Application Data

(63) Continuation of application No. 09/484,670, filed on Jan. 18, 2000, now Pat. No. 6,340,744.
(60) Provisional application No. 60/116,316, filed on Jan. 19, 1999.

(51) Int. Cl.⁷ ................................................ C12Q 1/00
(52) U.S. Cl. ............................ 435/4; 435/968; 435/960
(58) Field of Search ............................ 435/4, 968, 960

(56) References Cited

U.S. PATENT DOCUMENTS

| | | | |
|---|---|---|---|
| 5,316,909 A | 5/1994 | Xu | 435/6 |
| 5,373,093 A | 12/1994 | Vallarino et al. | 534/15 |
| 5,696,240 A | 12/1997 | Vallarino et al. | 514/15 |
| 6,107,024 A | 8/2000 | Schaap | 435/6 |
| 6,340,744 B1 * | 1/2002 | Leif et al. | 534/15 |

OTHER PUBLICATIONS

Adeyiga, A.M. et al., "Advances in the Development of Lanthanide Macrocyclic Complexes as Luminescent Bio–Markers", *Optical Diagnosis of Living Cells and Biolfuids*, SPIE Proceedings Series, vol. 2678, pp. 212–220 (1996).

Melentieva, E.V. et al., "The Analytical Use of the Fluorescence of the Four–Ligand B–Diketone Complexes of Europium and Samarium with Organic Bases", *Zh. Anal. Khim.*, vol. XXII, pp. 187–192 (1967).

Yang Jing–He et al., "Enhanced Luminescence of the Europium/Terbium/Thenoyltrifluoroacetone/1,10–Phenanthroline/Surfactant System, and its Analytical Application", *Anal. Chim. Acta*, vol. 198, pp. 287–292 (1987).

Jing–He Yang et al., "Application of the Co–Luminescence Effect of Rare Earths: Simultaneous Determination of Trace Amounts of Samarium and Europium in Solution", *Analyst*, vol. 114, pp. 1417–1419 (Nov. 1989).

(List continued on next page.)

Primary Examiner—Louise N. Leary
(74) Attorney, Agent, or Firm—Gary M. Nath; Joshua B. Goldberg; Nath & Associates PLLC

(57) ABSTRACT

Disclosed are a spectrofluorimetrically detectable luminescent composition and processes for enhancing the luminescence of one or more lanthanide-containing macrocycles. The luminescent composition comprises a micelle-producing amount of at least one surfactant, at least one energy transfer acceptor lanthanide element macrocycle compound having an emission spectrum peak in the range from 500 to 950 nanometers, and a luminescence-enhancing amount of at least one energy transfer donor compound of yttrium or a 3-valent lanthanide element having atomic number 59–71, provided that the lanthanide element of said macrocycle compound and the lanthanide element of said energy transfer donor compound are not identical. The addition of gadolinium(III) in the presence of other solutes to both the prototype and the di-functionalized europium, samarium, and terbium macrocyclic complexes, which were taught in our U.S. Pat. Nos. 5,373,093 and 5,696,240, enhances their luminescence. Similar enhancements of luminescence also results for the mono-functionalized europium, samarium, and terbium macrocyclic complexes, which were taught in our U.S. Pat. No. 5,696,240. The enhanced luminescence afforded by the composition enables the detection and/or quantitation of many analytes in low concentrations without the use of expensive, complicated time-gated detection systems.

24 Claims, 11 Drawing Sheets

OTHER PUBLICATIONS

Jinghe Yang et al., "Fluorescence Enhancement of the Eu–Tb–Benzoylacetone–Phenanthroline System", *Anal. Chim. Acta*, vol. 238, pp. 307–314 (1990).

Yong–Yuan Xu, "Co–fluorescence of Europium and Samarium in Time–Resolved Fluorometric Immunoassays", *Analyst*, vol. 116, pp. 1155–1158 (Nov. 1991).

Yun–Xiang Ci, "Fluorescence Enhancement of the Europium (III)–Thenoyltrifluoroacetone–Trioctylphosphine Oxide Ternary Complex by Gadolinium (III) and its Application to the Determination of Europium (III)", *Analyst*, vol. 113, pp. 1453–1457 (Sep. 1988).

Yun–Xiang Ci et al., "Enhanced Fluorometric Determination of Europium (III) with Thenoyltrifluoroacetone and 4,7–diphenyl–1,10–Phenanthroline by Gadolinium (III)", *Analytical Lett.*, vol. 21(8), pp. 1499–1513 (1988).

Yun–Xiang Ci et al., "Fluorometric Determination of Samarium and Gadolinium by Enhancement of Fluorescence of Samarium–Thenoyltrifluoroacetone–1,10–Phenanthroline Ternary Complex by Gadolinium", *Anal Chem.*, vol. 61, pp. 1063–1069 (1989).

Sabbatini, N. et al., "Radiative and Nonradiative Transitions in the Eu (III) Hexaaza Macrocyclic Complex [Eu(C22H26N6) (CH3COO)](CH3COO) C12H2O", *J. Phys. Chem.*, vol. 91, pp. 4681–4685 (1987).

Hemmila, I. et al., "Chap. 5, Time–Resolved Fluorometry, in Bioanalytical applications of labelling technologies, A review of trends and new opportunities in biospecific assay, based on the product offering of Wallac, and EG&G company", Edited by I. Hemmila et al. ISBN 951–9489–32–0 (1994).

Lempicki, A. et al., "Europium Chelates as Laser Materials", *Proceedings of the Fourth Conference on Rare Earth Research*, Apr. 22–25, 1964, LeRoy Eyring (ed.), Gordon and Breach, Science Publishers, pp. 351–361.

Quagliano, J.V. et al., *Coordination Chemistry*, Lexington, Mass, D C Heath and Company, 1969, p. 3.

Melson, G.A., *Coordination Chemistry of Macrocyclic Compounds*, New York, Plenum Press, 1979, pp. 2–5.

Lindoy, L.F., *The chemistry of macrocyclic ligand complexes*, Cambridge (UK), Cambridge University Press, 1989, pp. 1–4.

Leif, R.C. et al., "Rare Earth Chelates as Fluorescent Markers in Cell Separation and Analysis", *ACS Symposium Series 464m Cell Separation Science and Technology*, D S Kompala and P W Todd (eds.), American Chemical Society, Washington DC, 1991, pp. 41–58.

Benetollo, F. et al., "Structure of the [5S, 15S] isomer of the macrocyclic complex [La(NCS)$_3$ (C$_{24}$H$_{30}$N$_6$)]", *J. Chem. Crystallography*, vol. 26, pp. 9–13 (1996).

Vallarino, L., "Lanthanide (III) complexes of six–nitrogen–donor macrocyclic ligands with peripheral functionalities", *J. Alloys and Compounds*, vol. 249, pp. 69–75 (1997).

Benetollo, F. et al., "Constitutional isomers and stereoisomers of lanthanum (III) complex of the dimethyl–substituted six–nitrogen–donor ligand [La (C$_{24}$H$_{30}$N$_6$) (NCS)$_3$ (H$_2$O)]. 0.5 H$_2$O", *Polyhedron*, vol. 20, pp. 3622–3642 (1998).

* cited by examiner

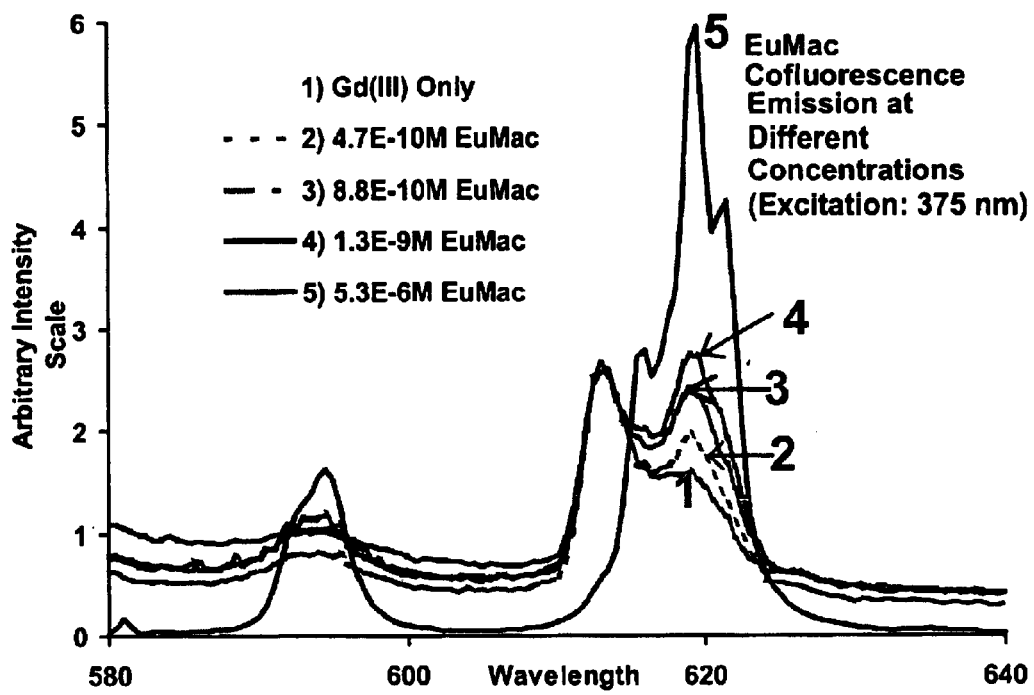
Figure 2
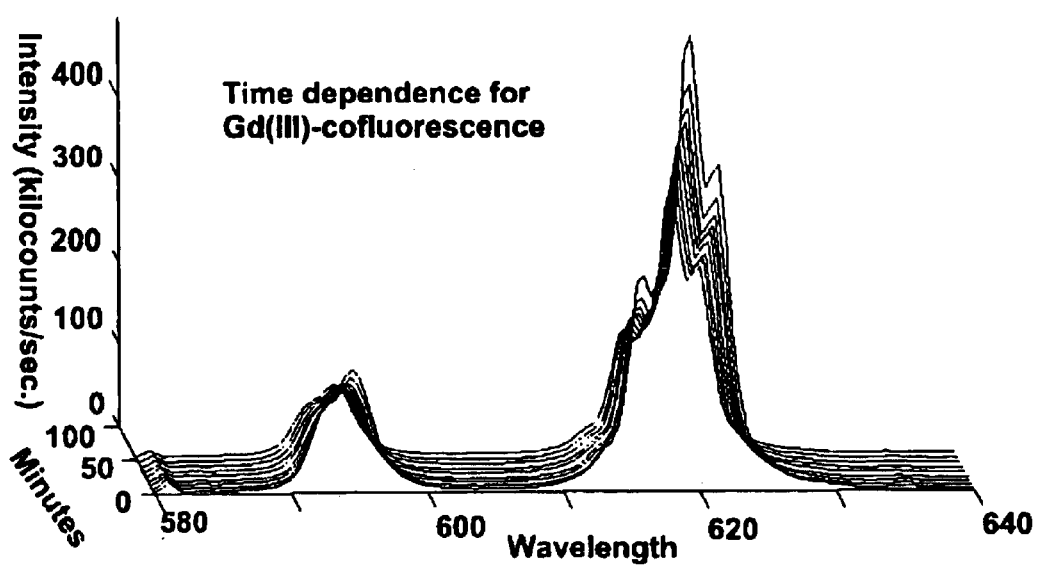
Figur 3

REAGENT SYSTEM AND METHOD FOR INCREASING THE LUMINESCENCE OF LANTHANIDE(III) MACROCYCLIC COMPLEXES

CROSS REFERENCES

This application is a Continuation of allowed application Ser. No. 09/484,670 filed Jan. 8, 2000 now U.S. Pat. No. 6,340,744 and claims the benefit of Provisional Application No. 60/116,316 filed on Jan. 19, 1999.

This invention, disclosed and/or claimed, was made with Government support under Small Business Technology Transfer Grant 5 R42 CA 73089 awarded by the National Institutes of Health, National Cancer Institute. The United States Government has certain rights in the invention."

BACKGROUND OF THE INVENTION

1. Field of the Invention

This invention relates to enhanced luminescence of covalently coupled dyes containing lanthanide macrocycle complexes, especially as tags for detecting members of combining pairs, and to the detection of low levels of these dyes.

2. Prior Art

The sensitivity of fluorescence measurements for the analysis of biological samples is often limited by background signal due to autofluorescence or Raman scattering.

At present, the microscopic visualization of luminescent labels containing lanthanide (III) ions, primarily europium (III), as light emitting centers is best performed with time-gated instrumentation, which by virtually eliminating the background fluorescence, results in an improved signal to noise ratio. Although the use of time-gated luminescence for microscopic and clinical chemistry analyses holds the promise of maximizing the detectability and quantitation of markers containing lanthanide complexes, this instrumentation is costly and not widely available; furthermore, time-gated measurements often involve loss of signal or precision. The combination of an image-intensifier coupled to a CCD permits the high speed gating of image acquisition. Briefly, rapid voltage changes at the intensifier dynodes result in concomitant changes in the current amplification, which effectively shutters the photoelectrons impinging on the phosphor that is located directly in front of the CCD surface. Other time-gating approaches to control the image acquisition of digital microscopes include high speed rotating choppers and ferro-electric shutters. However, none of these is suitable for the clinical pathology or clinical chemistry laboratory.

Vallarino and Leif U.S. Pat. Nos. 5,373,093 and 5,696,240 disclosed hexa-aza-macrocyclic complexes incorporating a lanthanide, actinide, or yttrium ion possessing high kinetic stability and pendant functional groups that can be readily coupled/conjugated to a biologically active molecule such as an antibody or antigen, or to a biologically compatible ionically uncharged macromolecule such as a linear or cross-linked polysaccharide. The complexes of europium (III) and terbium (III), for example, possess a long-lived fluorescence intensity that can be substantially increased by inter-action with a suitable enhancer, for example the sodium salt of dibenzoylmethane or thenoyltrifluoroacetyl-acetone. The entire disclosure of these patents is here incorporated by reference.

Xu U.S. Pat. No. 5,316,909 disclosed the interaction between B-diketonate complexes of luminescent lanthanide (III) and yttrium (III) in the presence of a synergistic compound to provide a cofluorescence effect which significantly increases the emission intensity. The embodiment described requires that the original chelate containing the fluorescent ion be dissociated from the biomolecule, followed by the addition of the yttrium cofluorescence species and incubation with the synergistic compounds for 1 to 15 minutes prior to measurement.

Adeyiga et al. SPIE vol. 2678, pages 212–220 (1996) disclosed extension of Xu's method to other lanthanide complexes including the europium (III) macrocycles. It is stated at page 215 that "a preliminary, unoptimized study with the parent unfunctionalized macrocycle {Eu $(C_{22}H_{26}N_6)$} triacetate complex as prototype has shown an approximate three fold increase in luminescence."

SUMMARY OF THE INVENTION

In accordance with this invention, there is provided a spectrofluorimetrically detectable luminescent composition comprising water, a micelle-producing amount of at least one surfactant, at least $1 \times 10^{-10}$ moles/liter of at least one energy transfer acceptor lanthanide element macrocycle compound having an emission spectrum peak in the range from 500 to 950 nanometers, and a luminescence-enhancing amount of at least one energy transfer donor compound of yttrium or a 3-valent lanthanide element having atomic number 59–71, provided that the lanthanide element of said macrocycle compound and the lanthanide element of said energy transfer donor compound are not identical.

The enhanced luminescence of compositions according to the invention permits the detection and/or quantitation of the lanthanide macrocycle compound and complexes thereof without the use of expensive and complicated time-gated detection systems. As a result, these macrocycle compounds and complexes thereof are useful as reporter molecules in immunoassays, analytical cytology, histological staining, and imaging processing.

The enhanced luminescence of compositions according to the invention caused by a different lanthanide energy transfer donor compound can also occur with functionalized derivatives of energy transfer acceptor lanthanide macrocycles, that is macrocycles substituted with reactive functional groups at which reaction with analytes can take place; with reaction products of such functionalized macrocycles with such analytes; and with polymers which contain multiple lanthanide-containing units. Through their reactive functional groups, functionalized energy transfer acceptor lanthanide macrocycles can be attached by a coupling functionality to analytes including small molecules of biological interest having molecular weights from 125 to 2000 daltons, such as nucleic acid bases or haptens, and large molecules of biological interest having molecular weights greater than 2000 daltons such as proteins including antibodies, polysaccharides, or nucleic acids.

Also in accordance with this invention, there is provided a method for analysis of a sample suspected of containing at least one analyte, frequently a biologically active compound, said method comprising:

a) contacting said sample with a functionalized complex of a metal M, where M is a metal ion selected from the group consisting of a lanthanide having atomic number 57–71, an actinide having atomic number 89–103 and yttrium(III) having atomic number 39;

in a reaction medium under binding conditions, whereby said analyte when present either interacts with said complex to form a conjugate or competes for interaction with a binding material specific for interaction with said complex and with said analyte;

b) adding to said reaction medium a luminescence-enhancing amount of at least one energy transfer donor compound of yttrium or a 3-valent lanthanide element having atomic number 59–71, provided that the lanthanide element of said macrocycle compound and a lanthanide element of said energy transfer donor compound are not identical, (c) subjecting said reaction medium to excitation energy in the range of 200–400 nm, whereby enhanced luminescence in the range of 500–950 nm is generated, (d) monitoring said luminescence of the reaction medium to measure in said sample at least one of the following:
  (1) presence and/or concentration of said conjugate;
  (2) presence and/or concentration of the product of the interaction of said complex with said binding material; and
  (3) presence and/or concentration of the product of the interaction of the conjugate with the binding material.

It is a feature of this invention that the method does not require prior dissociation of the luminescence-enhanced complex before measuring its emission spectrum. Moreover, since the excitation spectra of lanthanide macrocycles and those of several DNA-specific dyes, including 4',6-diamidino-2-phenylindole (DAPI) occur in the same region of the ultraviolet, both types of compounds can be excited at the same wavelength, while their emission spectra are very different. The organic dyes have broad emissions in the blue region of the spectrum while the enhanced luminescence of lanthanide macrocycles according to this invention occurs as very narrow emission peaks in the red. This difference allows the major emission of the enhanced luminescence composition of this invention to be unambiguously detected even when its intensity is much lower than that of the very strong emission of the DNA specific organic dyes.

It is a further feature of the invention that the composition and method of the invention not only provide enhanced luminescence but also minimize the interfering effect of non-specific binding of lanthanide metal macrocyclic compounds and complexes to substrates.

DESCRIPTION OF PREFERRED EMBODIMENTS

The lanthanide energy transfer acceptor macrocyclic compound ingredient of the composition of the invention is characterized by kinetic stability even in very dilute aqueous solution. The compound is resistant to removal or exchange of the central metal atom, and has a counterion or balancing anion readily exchanged for other anions. The term "lanthanide" is used throughout the specification and claims to refer to central atoms of yttrium (III) and 3-valent actinide atoms (atomic number 89–103) as well as to 3-valent central atoms of lanthanide elements of atomic number 57–71.

The lanthanide energy transfer acceptor macrocyclic compound ingredient of the composition of the invention is further characterized by the fluorescence spectrum with emission in the range from 500 to 950 nanometers upon excitation in the range from 200 to 400 nanometers.

The macrocycle of the lanthanide energy transfer acceptor macrocyclic compound has six coordinating atoms, of which at least 4 are nitrogen atoms, and the remainder are nitrogen, oxygen, or sulfur.

In particularly preferred compositions of the invention, the lanthanide energy transfer acceptor macrocyclic compound has the formula

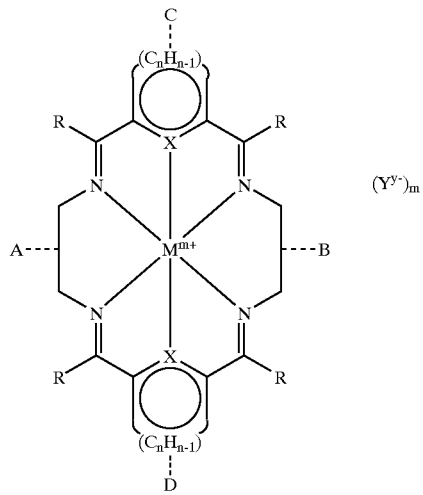

Formula I

Wherein

M is a metal ion selected from the group consisting of a lanthanide having atomic number 57–71, an actinide having atomic number 89–103 and yttrium(III) having atomic number 39;

R is a substituent selected from the group consisting of hydrogen, straight-chain alkyl, or branched-chain alkyl; aryl-substituted alkyl, aryl, and alkyl-substituted aryl, with the proviso that such substituent does not limit the solubility of the resultant complex or otherwise interfere with the cyclization of such complex during its synthesis;

X is selected from the group consisting of nitrogen, sulfur and oxygen which forms a part of a ring structure selected from the group consisting of pyridine, thiophene or furan, respectively, at the positions marked X;

n is 2 or 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex, and;

y is the ionic charge of the counterion in the macrocyclic complex.

A, B, C, and D are selected substituents selected from the group consisting of hydrogen, straight-chain alkyl, or branched-chain alkyl; aryl-substituted alkyl, aryl, or alkyl-substituted aryl; reactive functionality, functionalized alkyl, functionalized aryl-substituted alkyl, functionalized aryl, or functionalized alkyl-substituted aryl;

Straight chain and branched chain alkyl substituents at A, B, C, and/or D have from 1 to 25 carbon atoms. Reactive functionality signifies any substituent capable of reacting with a compound of biological interest to form a covalent bond, such as alcoholic hydroxyl, phenolic hydroxyl, aldehyde, carboxylic acid, carboxamide, halogen, isocyanate, isothiocyanate, mercapto and nitrile substituents. Functionalized alkyl, functionalized aryl-substituted alkyl, functionalized aryl, and functionalized alkyl-substituted aryl signify the respective alkyl; aryl-substituted alkyl, aryl, and alkyl-substituted aryl groups substituted with a reactive functionality thereby spaced from the macrocycle as desired. Thus, a 10 carbon alkyl chain at A, B, C, and/or D can bear a terminal aminophenyl group, further illustrative functionalized substituents include hydroxymethyl, 4-hydroxybenzyl, 4-aminobenzyl, and 4-isothiocyanatobenzyl.

For convenience, the following abbreviations can be used to refer to compounds of Formula I. Any and all of the lanthanide ions including those having atomic number 57–71, actinides having atomic number 89–103 and yttrium (III) having atomic number of 39 are represented by M. Specific metal ions are represented by their standard chemical abbreviation. The generic term MMac refers to any and all of the macrocyclic species of Formula I. The unfunctionalized, mono-functionalized, and di-functionalized macrocyclic complexes of Formula I are abbreviated respectively as: "Mac", "Mac-mono" and "Mac-di". When a specific peripheral pendant substituent having at least one reactive site (reactive functionality) is specified, its abbreviation is given as a suffix. Thus the compound of Formula I shown below, in which M is europium, each R is methyl (as shown by bond lines without termination) and each of A and B is a 4-isothiocyanatobenzyl group, is abbreviated as EuMac-di-NCS. The compound of Formula I shown below, in which M is terbium, each R is methyl, and B is a 4-isothiocyanatobenzyl group, is abbreviated as TbMac-mono-NCS, and the unfunctionalized compound of Formula I shown below, in which M is europium, each R is methyl and each of A and B is hydrogen, is abbreviated as EuMac.

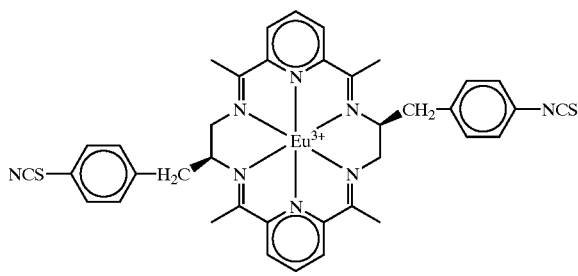

Formula II. Schematic formula of a di-functionalized europium macrocyclic complex. This structure is one of the isomers of the cationic europium macrocyclic moiety containing a 4-isothiocyanate-benzyl- substituent on each of the aliphatic side-chains. The molecular formula of the moiety is $C_{38}H_{36}N_5S_2Eu$. This and those that follow that include methyl groups adhere to the present convention of showing methyl groups as bond lines without termination.

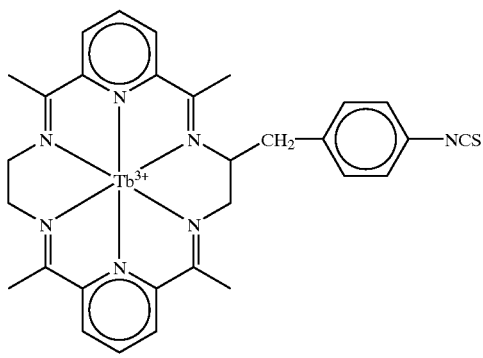

Formula III. Schematic formula of a cationic mono-functionalized terbium macrocyclic complex containing a 4-isothiocyanate-benzyl-substituent on one of the aliphatic side-chains, where the metal ion is terbium(III). The molecular formula of the moiety is $C_{30}H_{31}N_5STb$.

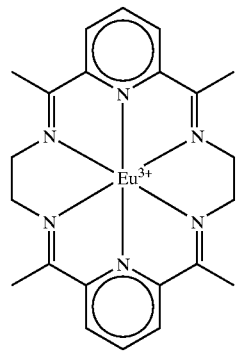

Formula IV. Schematic formula of a cationic unfunctionalized europium macrocyclic complex. This structure is the unfunctionalized prototype of the EuMac.

For the synthesis of these lanthanide element macrocycle compounds including access to the required starting materials, reaction conditions, purification, and subsequent coupling reactions with compounds of biological interest, reference can be had to Vallarino et al. U.S. Pat. Nos. 5,373,093 and 5,696,240 here incorporated by reference.

In a preferred group of compositions of this invention, at least one of the substituents A, B, C, and D of Formula I is a reactive functionality or a functionalized alkyl, functionalized aryl-substituted alkyl, functionalized aryl, or functionalized alkyl-substituted aryl group. Through these substituent groups, coupling or noncovalent binding can take place with an analyte, which can be a biologically active compound or any other compound able to interact with a functionalized substituent at A, B, C, and/or D.

Such coupling can take place directly, as in a conjugate of a MMac with a protein or a polynucleotide linked to the MMac through a functionalized group at A, B, C, or D.

Coupling of a functionalized group at A, B, C, or D with an analyte can also take place indirectly, by reaction of the functionalized group and a bridging/linking moiety providing the capability for derivatization with a receptor molecule or an entity for which there is a corresponding receptor molecule together with controlled spacing of the substrate of biological interest relative to the macrocycle of Formula I. Thus coupling is accomplished indirectly, either by the use of a bifunctional crosslinking reagent that provides covalent binding to the substrate of biological interest, or by binding the macrocycle to another molecule that has a high affinity for the substrate. To illustrate, avidin can couple with a functionalized macrocycle as well as with biotin, thus providing a link between biotin and the MMac. In another illustrative reaction, an amine-functionalized macrocyclic complex of Formula I is acylated with a reagent, such as bromoacetylbromide, to form the reactive bromoacetamide group which then readily alkylates free proteins to form the protein/macrocycle conjugate.

The noncovalent binding of these lanthanide element macrocycle compounds permits enhanced luminescence to be used with stains for proteins and other compounds. These stains can be used for electrophoresis including staining of gels that are predominantly composed of water. Other applications include fingerprint detection.

In a particularly preferred embodiment, a composition of the invention can include two different MMac each coupled to a polynucleotide as energy transfer acceptors, or two different MMac as energy transfer acceptors, each coupled to a different polynucleotide, and having luminescence enhanced according to the invention. When the different MMac differ in their central atoms, as with an europium macrocycle and a samarium macrocycle, and hence in emission peaks, measurement of the intensity of each peak provides a measure of the concentration of each MMac and of their relative ratios over a range from 500:1 to 1:500.

An important application of the above effect is the measurement of relative concentrations of normal cell DNA and cancer cell DNA by coupling each of these to a different MMac.

For further details of the coupling capabilities of functionalized macrocycles of Formula I reference can be made to Vallarino et al U.S. Pat. No. 5,696,240 at column 21 line 52 to column 22 line 42, here incorporated by reference.

When a functionalized macrocycle of Formula I is coupled directly or through a bridging/linking moiety to a reactive biomolecule, the resulting conjugate has the formula Formula V

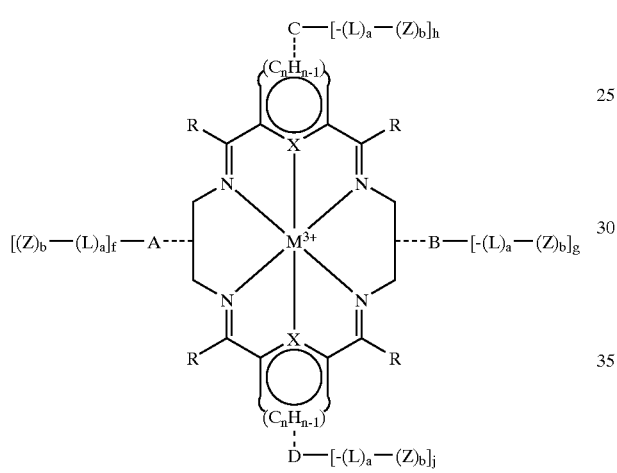

in which M, X, R, and n are as defined above; from one to two of A, B, C, and D are functionalized groups as defined above, and the remaining groups of A, B, C, and D are selected from the group consisting of hydrogen, straight-chain alkyl, branched-chain alkyl, aryl-substituted alkyl, aryl, and alkyl-substituted aryl; L is a bridging/linking moiety between the functionalized macrocycle and a biologically active compound, Z is a residue of a biologically active compound linked to L, a is zero or one, b is one, and each of f, g, h, and j is independently zero or one, provided that the sum of f, g, h, and j is either one or two.

When a functionalized macrocycle of Formula I is coupled to a bridging/linking moiety with the capability of further reacting with an analyte to form a conjugate, the resulting complex has Formula V in which L is a bridging/linking moiety capable of coupling the functionalized macrocycle and the analyte, a is one and b is zero, and M, X, R, n, A, B, C, D, f, g, h, and j are as defined above.

As a result of the ability of analytes including reactive biomolecules to bond to a functionalized macrocycle in a composition of this invention, as expressed by Z in Formula V, the enhanced luminescence of the composition can serve as an analytical tool for estimating such biomolecules as analytes. Thus the analyte can be any compound of interest, naturally occurring or synthetic, for which there exists a complementary binding partner.

These analytes are conveniently grouped by molecular weights. One group of such analytes consists of compounds that have molecular weights in the range of about 125–2,000 daltons and include a wide variety of substances, which are often referred to as haptens. These compounds include:
  (a) Vitamins, vitamin precursors, and vitamin metabolites including retinol, vitamin K, cobalamin, biotin, folate;
  (b) Hormones and related compounds including
    (i) steroid hormones including estrogen, corticosterone, testosterone, ecdysone,
    (i) aminoacid derived hormones including thyroxine, epinephrine,
    (i) prostaglandins,
    (i) peptide hormones including oxytocin, somatostatin,
  (c) pharmaceuticals including aspirin, penicillin, hydrochlorothiazide,
  (d) Nucleic acid constituents including
    (i) natural and synthetic nucleic acid bases including cytosine, thymine, adenine, guanine, uracil, derivatives of said bases including 5-bromouracil,
    (ii) natural and synthetic nucleosides and deoxynucleosides including 2-deoxyadenosine, 2-deoxycytidine, 2-deoxythymidine, 2-deoxyguanosine, 5-bromo-2-deoxyuridine, adenosine, cytidine, uridine, guanosine, 5-bromo uridine,
    (iii) natural and synthetic nucleotides including the mono, di, and triphosphates of 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine,
  (e) drugs of abuse including cocaine, tetrahydrocannabinol,
  (f) histological stains including fluorescein, DAPI
  (g) pesticides including digitoxin,
  (h) and miscellaneous haptens including diphenylhydantoin, quinidine, RDX.

Another group of analytes consists of compounds having a molecular weight of 2,000 daltons or more; including
  (a) proteins and their combinations including
    (i) albumins, globulins, hemoglobin, staphylococcal protein A, alpha-fetoprotein, retinol-binding protein, avidin, streptavidin, C-reactive protein, collagen, keratin,
    (ii) immunoglobulins including IgG, IgM, IgA, IgE,
    (iii) Hormones including lymphokines, follicle stimulating hormone, and thyroid stimulating hormone,
  (iv) enzymes including trypsin, pepsin, reverse transcriptases
  (v) cell surface antigens on T- and B-lymphocytes, i.e. CD-4, CD-8, CD-20 proteins, and the leukocyte cell surface antigens, such as described in the presently employed CD nomenclature;
    (vi) blood group antigens including A, B and Rh,
    (vii) major histocompatibility antigens both of class 1 and class 2,
    (viii) hormone receptors including estrogen receptor, progesterone receptor, and glucocorticoid receptor,
    (ix) cell cycle associated proteins including protein kinases, cyclins, PCNA, p53,
    (x) antigens associated with cancer diagnosis and therapy including BRCA(s) carcinoembryonic antigen, HPV 16, HPV 18, MDR, c-neu; tumor suppressor proteins, p53 and retinalblastoma,
    (xi) apoptosis related markers including annexin V, bak, bcl-2, fas caspases, nuclear matrix protein, cytochrome c, nucleosome, (xii) toxins including cholera toxin, diphtheria toxin, and botulinum toxin, snake venom toxins, tetrodotoxin, saxitoxin,
(xiii) lectins including concanavalin, wheat germ agglutinin, soy bean agglutinin,
(b) polysialic acids including chitin;
(c) polynucleotides including
(i) RNAs including segments of the HIV genome, human hemoglobin A messenger RNA,
(ii) DNAs including chromosome specific sequences, centromeres, telomere specific sequences, single copy sequences from normal tissues, single copy sequences from tumors.

The biomolecule to be coupled to the macrocyclic complex for imaging or therapy is typically one selected to carry out a specific target function. In one embodiment, the biomolecule is a monoclonal antibody or antibody fragment which is specific against a selected cell-surface target site. Such antibodies are commercially available, or are made by well-known techniques.

In a preferred embodiment, the lanthanide element of the energy transfer acceptor macrocyclic compound is europium, samarium, or terbium. In a particularly preferred embodiment, a composition of the invention includes an energy transfer acceptor macrocyclic compound in which the central atom is europium and a second energy transfer acceptor macrocyclic compound in which the central atom is samarium. The characteristic emission peaks of europium and samarium in the spectrum are sufficiently separated so that the two macrocyclic compounds can be measured in the presence of one another. As a result, two different biomolecules can be measured in the presence of one another by using an enhanced luminescence composition of the invention whereby one is coupled to a functionalized europium macrocycle and another is coupled to a functionalized samarium macrocycle.

Also in accordance with this invention, the enhanced luminescence of the composition of the invention is produced by the interaction in an aqueous micelle organization of an energy transfer acceptor lanthanide element macrocycle compound as defined above with a luminescence-enhancing amount of at least one energy transfer donor compound of yttrium or a 3-valent lanthanide element having atomic number 59–71, preferably a compound of yttrium, lanthanum, or gadolinium. The energy transfer donor compound is ionic and soluble in water.

The energy transfer donor compound in the composition is present in a concentration greater than the concentration of the energy transfer acceptor macrocycle compound. The concentration of the energy transfer donor compound can range from $1 \times 10^{-5}$ to $1 \times 10^{-3}$ moles per liter.

In a preferred composition according to the invention, the energy transfer donor compound is an ionic compound of or complex of gadolinium (III). The gadolinium (III) halides and especially gadolinium (III) trichloride are particularly preferred.

The enhanced luminescence composition of the invention is preferably adjusted to a pH in the range from 5.5 to 8.5, suitably by use of a buffer system. The buffer system is preferably free of multivalent inorganic anions such as borate, carbonate, and phosphate that can cause precipitation of the energy transfer acceptor compound from the solution. Preferred buffer materials include hexamethylenetetramine and tricine, both of which are commercially available.

The enhanced luminescence composition of the invention exists in a micellar organization. The importance of micellar organization to the enhanced luminescence composition is demonstrated by the observation that a water-miscible polar solvent such as ethanol when added to the characteristically cloudy and luminous composition completely discharges the luminescence and simultaneously turns the cloudy micellar liquid clear. Once formed in an aqueous micellar organization, the composition of the invention can be transferred to an immiscible non-aqueous medium and/or dried, as by evaporation or lyophilization, with preservation of its luminescence. To provide the micellar organization, the composition includes a micelle-forming amount of a surfactant.

Surfactants (a coined term derived from "surface active agent") are well known in the art and are organic compounds having a hydrophilic moiety and a hydrophobic moiety linked in the molecule. Surfactants are classified as amphoteric, anionic, cationic, or non-ionic according to the nature of the hydrophilic moiety; amphoterics include a hydrophilic anion, typically a carboxylate, sulfate, or sulfonate ion, and a hydrophilic cation, typically an ammonium ion; anionic and cationic surfactants include a hydrophilic ion of the respective type; and nonionic surfactants include an unionized hydrophilic group, typically a hydroxy (polyethylenoxy) group $(CH_2CH_2O)_pCH_2CH_2OH$ where p can range from 4 to about 30, preferably from 6 to 14, usually termed an "ethoxylate". Surfactants are further classified according to the hydrophobic moiety as alkyl, olefin, alkylbenzene, alkylphenol, polypropoxy etc.

Illustrative surfactants that can be used include cocoylamidopropylbetaine (amphoteric), household soap, lecithin, and dioctyl sodium sulfosuccinate (anionic), didodecyldimethylammonium chloride, cetylpyridinium bromide, and dodecylbenzylt-rimethylammonium chloride (cationic), glycerol monooleate, ethoxylated sorbitan monostearate, and ethoxylated nonylphenol (nonionic).

Cetyltrimethylammonium bromide, a cationic surfactant, is used in the preferred embodiment. The preferred concentrations for this surfactant range from $1.0 \times 10^{-4}$ to $1.0 \times 10^{-6}$ mol/L.

For a convenient compilation of many cationic surfactants reference can be had to McAtee U.S. Pat. No. 5,607,980 at column 7 line 55 to column 9 line 24, which disclosure is here incorporated by reference.

The concentration of surfactant is sufficient to form the micellar organization and thus typically exceeds the critical micelle concentration (CMC). The CMC has been measured and published for many surfactants. The suitable concentration of a surfactant whose CMC is not known is readily determined by incremental addition of the surfactant to a composition containing all the other intended ingredients until enhanced luminescence is observed.

In addition to the above disclosed energy transfer acceptor macrocycle compound, energy transfer donor compound, surfactant, and buffer ingredients, the composition of the invention can also contain one or more synergistic ligands to increase the luminescence of the composition beyond that attainable in absence of synergistic ligand. Such ligands do not displace the macrocycle of the acceptor or release the metal from the macrocycle and are presently believed to act by coordinating additional ligands to both acceptor (Eu or Sm or Tb and donor (Gd or Y, or La) in available spaces in the coordination sphere and thus prevent access of water that would cause vibrational quenching of the acceptor and/or donor.

Preferred synergistic ligands include trioctylphosphine oxide and 1,10-phenanthroline. The concentration of synergistic ligand when present can range from $10^{-3}$ to $10^{-6}$ moles/liter.

Moreover, the composition of the invention can contain one or more betadiketones. The concentration of betadiketone when present can range from $1\times10^{-2}$ to $1\times10^{-5}$ moles per liter. Preferred betadiketones have the formula RfCOCH$_2$COQ in which Rf is a perfluoroalkyl group having 1 to 8 carbon atoms and Q is a carbocyclic or heterocyclic aromatic group or an alkyl group having 1 to 11 carbon atoms. A particularly preferred betadiketone is thenoyltrifluoroacetone.

The reaction medium in which a sample containing or suspected of containing an analyte is contacted with a functionalized macrocyclic complex according to this invention is preferably an aqueous solution in which the presence of foreign materials such as salts or organic solvents is limited to such concentrations as are tolerated by the analyte without denaturation, degradation, coagulation, hydrolysis, polymerization or other interfering changes. Binding conditions include such conditions of temperature, pressure, and pH as favor the reaction of the analyte with the functionalized macrocyclic complex, preferably a temperature in the range from 10° C. to 45° C., a pressure in the range from 800 to 1000 millibars, and a pH in the range from 5.5 to 8.5.

The functionalized metal complex according the method of the invention is characterized by kinetic stability even in very dilute aqueous solution. The complex is resistant to removal or exchange of the central metal atom, and has a counterion or balancing anion readily exchanged for other anions. The central metal atom is a lanthanide metal atom which can be yttrium (III), a 3-valent actinide atoms (atomic number 89–103), as well as a 3-valent central atom of a lanthanide elements of atomic number 57–71.

The functionalized metal complex according to the method of the invention is further characterized by the fluorescence spectrum with emission in the range from 500 to 950 nanometers upon excitation in the range from 200 to 400 nanometers.

In a preferred embodiment, the lanthanide element of the functionalized macrocyclic metal complex is europium, samarium, or terbium. In a particularly preferred embodiment, a functionalized macrocyclic metal complex of europium and a functionalized macrocyclic metal complex of samarium are used in combination in the method according to the method of the invention. The characteristic emission peaks of europium and samarium in the spectrum are sufficiently separated so that the two macrocyclic complexes can be measured in the presence of one another. As a result, two different analytes can be measured in the presence of one another by the method of the invention whereby one is coupled to a functionalized europium macrocycle complex and another is coupled to a functionalized samarium macrocycle complex.

The macrocycle of the functionalized metal complex according to the method of the invention has six coordinating atoms, of which at least 4 are nitrogen atoms, and the remainder are nitrogen, oxygen, or sulfur.

In a particularly preferred embodiment, the functionalized metal complex according to the method of the invention has the formula

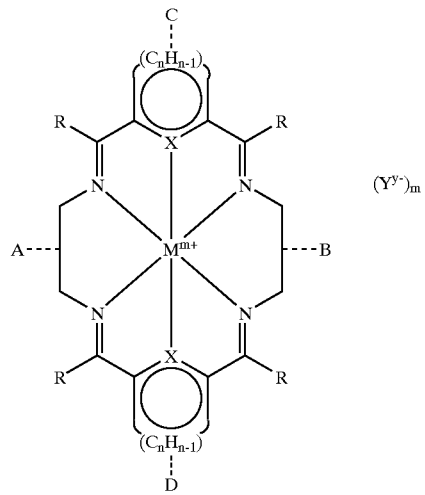

Formula I

Wherein

M is a metal ion selected from the group consisting of a lanthanide having atomic number 57–71, an actinide having atomic number 89–103 and yttrium(II) having atomic number 39;

R is a substituent selected from the group consisting of hydrogen, straight-chain alkyl, or branched-chain alkyl; aryl-substituted alkyl, aryl, and alkyl-substituted aryl, with the proviso that such substituent does not limit the solubility of the resultant complex.

X is selected from the group consisting of nitrogen, sulfur and oxygen which forms a part of a ring structure selected from the group consisting of pyridine, thiophene or furan, respectively, at the positions marked X;

n is 2 or 3;

Y is a negatively charged ion, including acetate, carboxylate, sulfonate, halide, nitrate, perchlorate, thiocyanate, and picrate, with the proviso that such negative ion does not limit the solubility of the resultant complex or otherwise interfere with either the coupling procedure or the energy transfer leading to fluorescence;

m is the ionic charge of the metal ion in the macrocyclic complex, and;

y$^-$ is the ionic charge of the counterion in the macrocyclic complex.

A, B, C, and D are substituents selected from the group consisting of hydrogen, straight-chain alkyl, or branched-chain alkyl; aryl-substituted alkyl, aryl, or alkyl-substituted aryl; reactive functionality, functionalized alkyl, functionalized aryl-substituted alkyl, functionalized aryl, or functionalized alkyl-substituted aryl;

at least one and not more than two of the substituents A, B, C, and D are selected from the group consisting of a reactive functionality, functionalized alkyl, functionalized aryl-substituted alkyl, functionalized aryl, or functionalized alkyl-substituted aryl, with the proviso that groups of said substituent provide coupling functionality between said substituent and a bridging/linking moiety to permit the derivatization thereof with a receptor molecule or an entity for which there is a corresponding receptor molecule;

and the remaining substituents A, B, C, and D are selected from the group consisting of reactive functionality, functionalized alkyl, functionalized aryl-substituted alkyl, functionalized aryl, or functionalized alkyl-substituted aryl, and groups that permit the coupling of the macrocycle to the biosubstrate, while also providing additional features such as increased solubility, greater stability, enhanced luminescence, or a combination thereof.

Straight chain and branched chain alkyl substituents at A, B, C, and/or D have from 1 to 25 carbon atoms. Reactive functionality signifies any substituent capable of reacting with a biologically active compound to form a covalent bond, such as alcoholic hydroxyl, phenolic hydroxyl, aldehyde, amino, carboxylic acid, carboxamide, isocyanate, isothiocyanate, mercapto and nitrile substituents. Functionalized alkyl, functionalized aryl-substituted alkyl, functionalized aryl, and functionalized alkyl-substituted aryl signify the respective groups substituted with a reactive functionality. Illustrative functionalized substituents include hydroxymethyl, 4-hydroxybenzyl, 4-aminobenzyl, and 4-isothiocyanatobenzyl.

Through these substituent groups, coupling can take place with an analyte. Such coupling can take place directly, as in a conjugate of a MMac with a protein or a polynucleotide linked to the MMac through a functionalized group at A, B, C, or D.

Coupling of a functionalized group at A, B, C, or D with an analyte can also take place indirectly, by reaction of the functionalized group and a bridging/linking moiety providing the capability for derivatization with a receptor molecule or an entity for which there is a corresponding receptor molecule together with controlled spacing of the analyte relative to the macrocycle of Formula I. Thus coupling is accomplished indirectly, either by the use of a bifunctional crosslinking reagent that provides covalent binding to the analyte, or by binding the macrocycle to another molecule that has a high affinity for the analyte. To illustrate, the bifunctional crosslinking reagent can be a protein or protein derivative capable of binding biotin, such as avidin or streptavidin, thus providing a link between biotin and the Mmac. In another illustrative reaction, an amine-functionalized macrocyclic complex of Formula I is acylated with a reagent, such as bromoacetylbromide, to form the reactive bromoacetamide group which then readily alkylates free proteins to form the protein/macrocycle conjugate.

When a functionalized macrocycle of Formula I is coupled directly or through a bridging/linking moiety to an analyte, the resulting conjugate has the formula

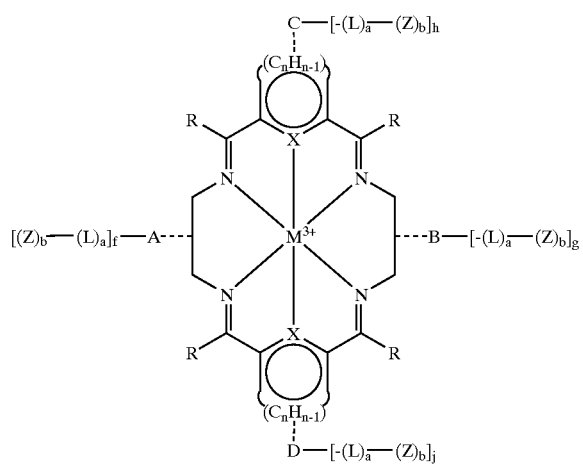

Formula V in which M, X, R, and n are as defined above; from one to two of A, B, C, and D are functionalized groups as defined above, and the remaining groups of A, B, C, and D are selected from the group consisting of hydrogen, straight-chain alkyl, branched-chain alkyl, aryl-substituted alkyl, aryl, and alkyl-substituted aryl; L is a bridging/linking moiety between the functionalized macrocycle and an analyte, Z is a residue of a biologically active compound linked to L, a is zero or one, b is one, and each of f, g, h, and j is independently zero or one, provided that the sum of f, g, h, and j is either one or two.

When a functionalized macrocycle of Formula I is coupled to a bridging/linking moiety with the capability of further reacting with an analyte to form a conjugate, the resulting complex has Formula V in which L is a bridging/linking moiety capable of coupling the functionalized macrocycle and an analyte, a is one and b is zero, and M, X, R, n, A, B, C, D, f, g, h, and j are as defined above.

A variety of instruments is commercially available according to this invention for monitoring the presence and/or concentration of the conjugate of a functionalized macrocyclic metal complex with an analyte, the presence and/or concentration of the product of the interaction of a functionalized macrocyclic metal complex with a binding material; and the presence and/or concentration of the product of the interaction of the conjugate with the binding material.

Time-gated fluorescence instrumentation can be used according to this invention, while equally effective and less expensive fluorescence instrumentation equipped with a continuous as opposed to pulsed light source can now be used as a result of this invention. Such instrumentation can include a standard manual or automated fluorometer for reading samples. Also suitable is fluorescence instrumentation that measures multiple samples at a time, having a luminescence detection zone in which multiple samples can be automatically positioned. Such instrumentation can include a microtiter plate or strip positioning system.

Among preferred continuous light source fluorescence instruments of these types can be mentioned SPEX 1692T spectrofluorometer manufactured by Instruments SA Spex Fluorescence Division and LS-50B Luminescence Spectrophotometer manufactured by Perkin Elmer LLC, 761 Main Avenue, Norwalk, Conn. 06859-0010 USA.

In a particularly preferred type of fluorescence instrumentation, the instrument includes the capability to image the sample being analyzed, and especially to measure the analyte at various points in the image. This can be accomplished in particular as the instrument measures, records, processes, and/or displays the spatial distribution of one or more analytes. Instrumentation with these capabilities include Chromoscan manufactured by Applied Imaging Corporation 2380 Walsh Avenue, Santa Clara, Calif. 95051 and Axioplan 2 imaging manufactured by Carl Zeiss, Inc. One Zeiss Drive Thornwood, N.Y. 10594.

Particularly preferred applications of the method include comparative genomic hybridization and measurement of one or more samples for an analyte on a microarray.

In an important extension of the method of the invention, the enhanced fluorescence composition of the invention formed in an aqueous micellar organization can be dried and/or transferred into a non-aqueous medium and measured in the non-aqueous environment or in the dry state.

The following examples, of compositions characterized by kinetic stability and containing a metal compound resistant to removal or exchange of the central metal atom, and their use, are provided by way of illustration and not of limitation of the invention, whose scope is defined by the appended claims.

BRIEF DESCRIPTION OF THE DRAWINGS

FIG. 2 is a graphical presentation of five emission spectra in the range from 580 to 640 nm.

FIG. 3 is a graphical presentation of the time dependence of an emission spectrum in the range from 580 to 640 nm.

Figure 1:
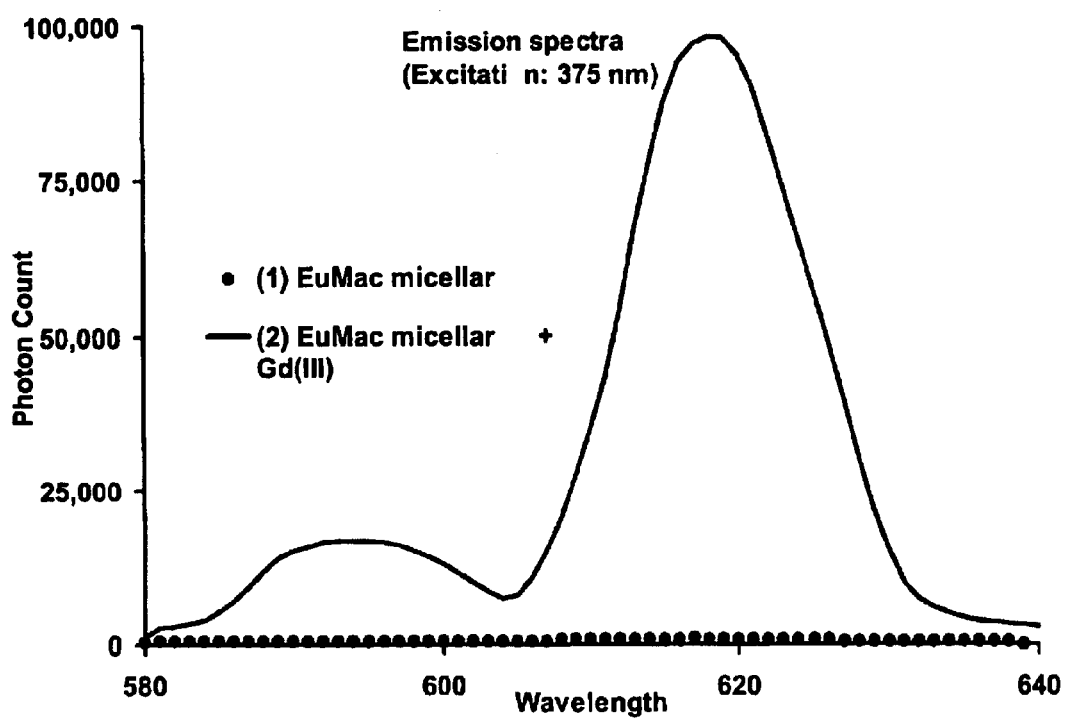
FIG. 1 is a graphical presentation of two emission spectra in the range from 580 to 640 nm.

SUMMARY OF EQUIPMENT INSTRUMENTS, MATERIALS, AND GENERAL PROCEDURES USED IN THE EXAMPLES

Equipment and Instruments.

All glassware was cleaned with a methanol/concentrated hydrochloric acid mixture (90/10 v/v), rinsed with deionized water and methanol, and dried at 60° C. Routine atomic absorption analyses of europium, samarium and terbium were performed on a Varian SpectraAA instrument, using as reference the elemental standards from Aldrich Chemical Co.; selected samples were analyzed by ICP-AES (Schneider Laboratories, Richmond, Va.). For fluorescence measurements, solutions were examined in stoppered triangular quartz cuvettes, so oriented that the excitation beam entered the diagonal face at a 45 degree angle and the emitted light was collected through the bulk of the sample at 90 degrees relative to excitation. All experiments and measurements were performed at ambient temperature unless stated otherwise.

The spectra obtained are presented in the graphs of FIG. 1 to FIG. 13

EXAMPLE I

Enhancement of the EuMac Luminescence by Gd (III) in Aqueous Micellar Solutions Containing Appropriate Additives

A. MATERIALS.

List 1:

(a) Cetyltrimethylammonium bromide (CTAB), commercially available from Aldrich Chemical Co., Catalog No. 85,582-0 (1996–1997), $1.00 \times 10^{-3}$ M in water.

(b) Hexamethylenetetramine, ACS Reagent (HMTA), commercially available from Aldrich Chemical Co., Catalog No. 39,861-0 (1996–97). Two solutions were used: (1) 10% m/v, 0.71 M in water, adjusted to pH 6.0 with hydrochloric acid (HMTA buffer pH 6.0); (2) 10% m/v, 0.71 M in water (HMTA base).

(c) 1,10-phenanthroline (PHEN), commercially available from Aldrich Chemical Co., Catalog No. 13,137-7 (1996–97), $5.50 \times 10^{-3}$ M in ethanol.

(d) Trioctylphosphine oxide (TOPO), commercially available from Aldrich Chemical Co., Catalog No. 22,330-1 (1996–97), $5.00 \times 10^{-3}$ M in ethanol.

(e) 4,4,4-trifluoro-1 (2-thienyl)-1,3-butanedione (thenoyltrifluoroacetone, HTTFA), commercially available from Aldrich Chemical Co., Catalog No. T2,700-6 (1996–97). The compound was purified by recrystallization from ethanol(charcoal)/hexane and stored at 4° C. in a dark glass container. The stock solution was $1.00 \times 10^{-2}$ M in ethanol.

(f) [Eu-macrocycle(acetate)$_2$](acetate), EuMac prepared as previously by De Cola et al. Inorganic Chemistry Vol. 25, 1729–1732 (1986), $2.3 \times 10^{-5}$ M in ethanol.

(g) Gd(III) chloride, $1 \times 10^{-3}$ M in water, was obtained from the oxide (99.999%, REO), commercially available from Alfa Aesar, catalog No. 11289 (1999–2000). The oxide, $Gd_2O_3$ ($5.00 \times 10^{-4}$ mol), was dissolved in a minimal volume of 15% hydrochloric acid with mild heating. The resulting solution was evaporated to dryness under reduced pressure and the white crystalline product thus obtained was dissolved in water to a total volume of 100 mL.

(h) Eu(III) chloride hexahydrate, 99.99% (commercially available from Aldrich Chemical Co., Catalog No. 20,235-4 (1996–97), $4.00 \times^{-6}$ M in water, was used as primary stock from which more dilute solutions were made as necessary.

List 2:
(a) Triton X-100 ethoxylated nonylphenol, commercially available from Aldrich Chemical Co., Catalog No. 23,472-9 (1996–97), 2% m/v stock solution in water.
(b) N-[tris(hydroxymethyl)]methylglycine (Tricine), commercially available from Aldrich Chemical Co., Catalog No. 16,378-3 (1996–97), 10% m/v (0.56 M) stock solution in water, adjusted to pH 6.2 with hydrochloric acid (tricine buffer).
(c) 4,4,4-trifluoro-1 (2-furyl)-1,3-butanedione (HTFFA), commercially available from Aldrich Chemical Co., Catalog No. 42,601-6 (1996–97), $1.0\times10^{-2}$ M stock solution in ethanol;
(d) 4,4,4-trifluoro-1 (2-naphthyl)-1,3-butanedione (HTFNA), commercially available from Aldrich Chemical Co., Catalog No. 34,363-3 (1996–97), $1.00\times10^{-2}$ M stock solution in ethanol;

All studies employed: surfactant, buffer, synergistic ligands, diketones, macrocyclic complex, and gadolinium trichloride. The materials listed above in List 1 were those used in the preferred embodiment of this example.

B. Procedure

In a series of experiments intended to determine the conditions of optimized luminescence described below, the EuMac or $EuCl_3$ concentration was kept constant ($2.3\times10^{-7}$M); this value was chosen to provide a range of luminescence intensities suitable for measurement with the SLM-8000 instrument. In the preferred embodiment, the buffer was HMTA pH 5.9–6.4; the surfactant was cetyltrimethylammonium bromide (CTAB), the synergistic ligands were 1,10-phenanthroline (PHEN) and trioctylphosphine oxide (TOPO); the enhancer was thenoyltrifluoroacetone (HTTFA); the macrocyclic complex was [Eu-macrocycle (acetate)$_2$](acetate) (EuMac); and the energy transfer donor was gadolinium trichloride. (These are the materials in List 1 above). Various concentrations of each component were tested; the pH of the final solution was kept in the 5.9–6.4 range.

In other experiments that also produced luminescence enhancement, the buffer was tricine, the surfactant Triton X-100, and the enhancer was either 4,4,4-trifluoro-1(2-furyl)-1,3-butanedione (HTFFA) or 4,4,4-trifluoro-1(2-naphthyl)-1.3-butanedione (HTFNA). (These are the materials in List 2 above). All other reagents were the same as in the preferred embodiment.

The following is an example of the protocol used for the preparation of a 5-mL sample of an optimized-cofluorescence solution of EuMac with Gd(III) as the energy transfer donor. All reagents were used in the form of the stock solutions given under MATERIALS, all volumes were measured with calibrated micropipets. In a glass vial, the following are mixed: 0.080 mL of PHEN, 0.050 mL of CTAB, 0.800 mL of HMTA buffer, 0.400 mL of HMTA base, 0.600 mL of $GdCl_3$, a measured volume (V mL) of the solution containing the EuMac, and the volume of water required to bring to total volume of the mixture to 5.00 mL after all components are added. Since the total volume of all fixed components is 2.410 mL, the volume of water to be added is [5.000–(2.410+V)] mL. The HTTFA (0.400 mL) is then added with gentle shaking and the previously clear solution becomes slightly cloudy owing to the formation of micelles. The micellar solution is allowed to stand at room temperature for 15–30 min, after which time 0.080 mL of TOPO are added and the cloudiness of the solution becomes more pronounced. The mixture is incubated for an additional 5 min; it is then placed in a quartz cell and its luminescence is obtained without further delay under the instrumental condition indicated in the section, Equipment and Instruments. The concentrations of all components in the final cofluorescence solution are listed in Table 1; minor variations (±5%) in the concentration of any component except the EuMac do not affect the luminescence intensity of the solution.

TABLE 1

Concentrations of Components in an Optimized Cofluorescence Solution Containing EuMac as the Emitting species and Gd(III) as the Energy Transfer Donor.

| Component | Moles/L |
| --- | --- |
| 1,10-Phenanthroline | $8.80 \times 10^{-5}$ |
| Cetyltrimethylammonium bromide | $1.00 \times 10^{-5}$ |
| Hexamethylenetetramine buffer | $1.14 \times 10^{-1}$ |
| Hexamethylenetetramine base | $5.68 \times 10^{-2}$ |
| 1,1,1-trifluoro-4(2-Thienyl)-2,4-butanedione (Thenoyltrifluoroacetone) | $8.00 \times 10^{-4}$ |
| Trioctylphosphine oxide | $8.00 \times 10^{-5}$ |
| Gd(III) chloride | $1.20 \times 10^{-4}$ |
| EuMac | $2.30 \times 10^{-7}$ |

In the following, as well as in other Examples, any solution containing the first six components shown in Table 1, at the concentrations listed in the Table, will be referred to as an "optimized cofluorescence matrix".

The emission spectra were obtained with the SLM-8000 instrument. Slits (both excitation and emission) were set at 16 mm for the SLM instrument, unless stated otherwise. All experiments and measurements were performed at ambient temperature. For comparison, the luminescence of EuMac in the optimized cofluorescence matrix, but without added Gd(III), was also measured under the same instrumental conditions.

FIG. 1 shows emission spectra (Excitation: 375 nm) of: (1) A solution of [Eu-macrocycle(acetate)$_2$](acetate) ($2.3\times10^{-7}$ M) in the optimized-cofluorescence matrix without Gd(III). (2) An identical solution but with Gd(III) chloride ($1.2\times10^{-4}$ M). In (2), the integrated emission intensity between 613 and 623 nm is increased over 100-fold by the addition of Gd(III).

The luminescence enhancement, or "cofluorescence", caused by the presence of Gd(III) is clearly illustrated in FIG. 1.

It should be emphasized that the cofluorescence effect requires that both the EuMac and the Gd(III) species be present in an aqueous micellar (slightly cloudy) solutions; the organization provided by the micellar system is essential to the energy transfer that leads to increased light emission by the EuMac. Thus, cofluorescence does not occur for "true" solutions in organic solvents and the addition of ethanol or other water-miscible organic solvent to a glowing (and cloudy) cofluorescent solution instantly destroys the luminescence enhancement as it turns the solution clear.

EXAMPLE II

Determination of the Limit of Detection of the EuMac by Gd(III)-Cofluorescence and Nature of the Emitting Species.

A. Materials

Except as otherwise stated, the Gd-containing optimized cofluorescence matrix of EXAMPLE I was used for this and the following examples. The $GdCl_3$ used in these solutions was synthesized from a gadolinium oxide containing approximately 0.3 ppm of europium by mass. Accordingly, the optimized cofluorescence solution of Table 1, EXAMPLE I, with $1.2 \times 10^{-4}$ mol/L of $GdCl_3$, contained approximately $4 \times 10^{-11}$ mol/L of Eu(III) as contaminant. The emission intensity produced by this Eu(III) contaminant under intrinsic cofluorescence conditions is negligible, relative to that of the EuMac, when the concentration of the latter is sufficiently high. At very low EuMac concentrations, however, the emission of the Eu(III) contaminant may become comparable to, and eventually higher than, the emission of the EuMac, thus posing a limit to its detection.

B. Procedure

The concentrations of EuMac was varied as appropriate, while the composition of the solution was kept constant. The emission spectra of solutions were obtained with a SPEX 1692T spectrofluorometer. The slits of the SPEX instrument were varied as required. All experiments and measurements were performed at ambient temperature unless stated otherwise.

Five Gd(III)-containing optimized cofluorescence solutions were prepared according to the general protocol described in EXAMPLE I. One of these solutions did not contain any EuMac or any other added compound of europium; the other solutions contained increasing concentrations of the EuMac. The spectra of the solutions were obtained with a SPEX 1692T spectrofluorometer, programmed for very high resolution in order to detect the presence of peaks corresponding to the $^5D_0 \rightarrow {}^7F_2$ emissions of different europium species, and also to reveal the peak pattern of this transition, which is characteristic of the coordination geometry of the emitter.

FIG. 2 shows the emission spectra (excitation, 375 nm) of cofluorescence-optimized solutions containing "free" Eu(III) (approximately $4 \times 10^{-11}$ M) as contaminant in the Gd(III) and the [Eu-macrocycle(acetate)$_2$](acetate) at four different concentrations, $4.7 \times 10^{-10}$ M, $8.8 \times 10^{-10}$ M, $1.3 \times 10^{-9}$ M, and $5.3 \times 10^{-6}$ M. The peak maximum for the $^5D_0 \rightarrow {}^7F_2$ transition is 614 nm for the Eu(III) contaminant and 619 nm for the Eu-macrocycle. Because they had the same Eu(III) contaminant, spectra 1 to 4 were normalized to the same peak height at 614 nm. Spectrum 5 (the highest concentration of the Eu-macrocycle) was scaled to permit comparison of the spectra.

As illustrated in FIG. 2, it was established that the $^5D_0 \rightarrow {}^7F_2$ band of the EuMac has a maximum at 619 nm, whereas that of the Eu(III) ion present as contaminant in the Gd(III) solution has a maximum at 614 nm. Thus, the high-resolution emission spectra of the two species can be unambiguously distinguished, and their intensities can be independently measured, as long as the EuMac is present in concentration appreciably greater than the Eu(III) contaminant. The latter condition is dictated by the fact that the emission intensity of the cofluorescence-enhanced Eu(III) is higher than that of the EuMac at the same concentration. Owing to these factors, the current limit of detection for the EuMac under Gd(III)-cofluorescence conditions lies between $1.0 \times 10^{-9}$ M and $5.0 \times 10^{-10}$ M When reporting the enhancement caused by Gd(III) on the luminescence emission of the EuMac or of any other Eu-macrocycle, it is necessary to keep in mind that at present even the purest commercially available gadolinium is contaminated by traces of Eu(III). This is a consequence of the fact that the two elements are obtained from the same minerals and that, being adjacent members of the Lanthanide Series, they are essentially identical in all properties except those related to the electronic configuration of their 4f electrons. The extreme similarity in the chemical behaviors and macroscopic physical properties of the two elements makes their separation from naturally occurring mixtures extremely difficult.

The results summarized above provide an insight on the nature of the luminescent species present in the Gd(III)-containing cofluorescence solutions of EuMac. The Eu(III) contaminant is most likely present as a mixture of [Eu(TTFA)$_3$(phen)] and [Eu(TTFA)$_3$(TOPO)$_2$] species. In turn, the Eu-macrocycle emitter is unambiguously identified as a single cationic species of formula [Eu-macrocycle (TTFA)$_2$]$^+$ on the basis of the following evidence (1) Only one emission corresponding to the $^5D_0 \rightarrow {}^7F_0$ transition occurs in the 580 nm region of the spectrum. (see also the far left of FIG. 3). (2) The entire spectrum, and in particular the pattern of the $^5D_0 \rightarrow {}^7F_2$ transition at 619 nm, is identical to that of the [Eu-macrocycle(acetate)$_2$](acetate) in an ethanol solution containing the diketone HTTFA as the sole additive. The structure of the species present in this ethanol solution was conclusively established by $^1$H NMR spectroscopy.

EXAMPLE III

Time-Dependence of the Luminescence Intensity of EuMac in Optimized Gd-Containing Cofluorescence Solutions and Nature of the Emitting Species A. Procedure.

The emission intensity of EuMac in the optimized Gd-cofluorescence solution was examined over a period on 1.5 hr. Solutions were prepared according to the protocol described in EXAMPLE I; spectra were recorded on the SPEX 1692T instrument as described in EXAMPLE II.

FIG. 3 is a time-dependence plot for the emission intensity of the [Eu-macrocycle(acetate)$_2$](acetate) complex in a Gd-containing optimized cofluorescence solution. Only one band arising from the $^5D_0 \rightarrow {}^7F_0$ transition of the Eu-macrocycle transition occurs at ca. 580 nm, showing that only one emitting species is present. Furthermore, the peak pattern of the band corresponding to the $^5D_0 \rightarrow {}^7F_2$ transition is constant in time, even though the intensity decreases, showing that the chemical nature of the emitting species remains unchanged.

The time dependence was not consistently reproducible, even for solutions of identical compositions. In some experiments the intensity remained approximately constant, and in others it first increased slightly and then gradually decreased. A screening of the influence of the synergistic ligands, 1,10-phenanthroline and trioctylphosphine oxide, showed that they have a somewhat stabilizing effect, in the sense that the variation of the luminescence intensity with time is more erratic when either is missing from the solution.

The graph of FIG. 3 illustrates a significant aspect of the cofluorescence time-dependence. The intensity of the emission spectrum changes with time, but the pattern of the spectrum—the "signature" of the emitting species—remains unchanged. This shows that there is no decomposition or rearrangement of the Eu-macrocycle emitter; the variation in emission intensity is the result of the dynamic character of micellar solutions. This is further confirmed by the observation that the micellar cofluorescence solution will, over a period of one-two days, spontaneously separate into a highly luminescent precipitate and a clear, non-luminescent solution.

EXAMPLE IV

Figure 4:
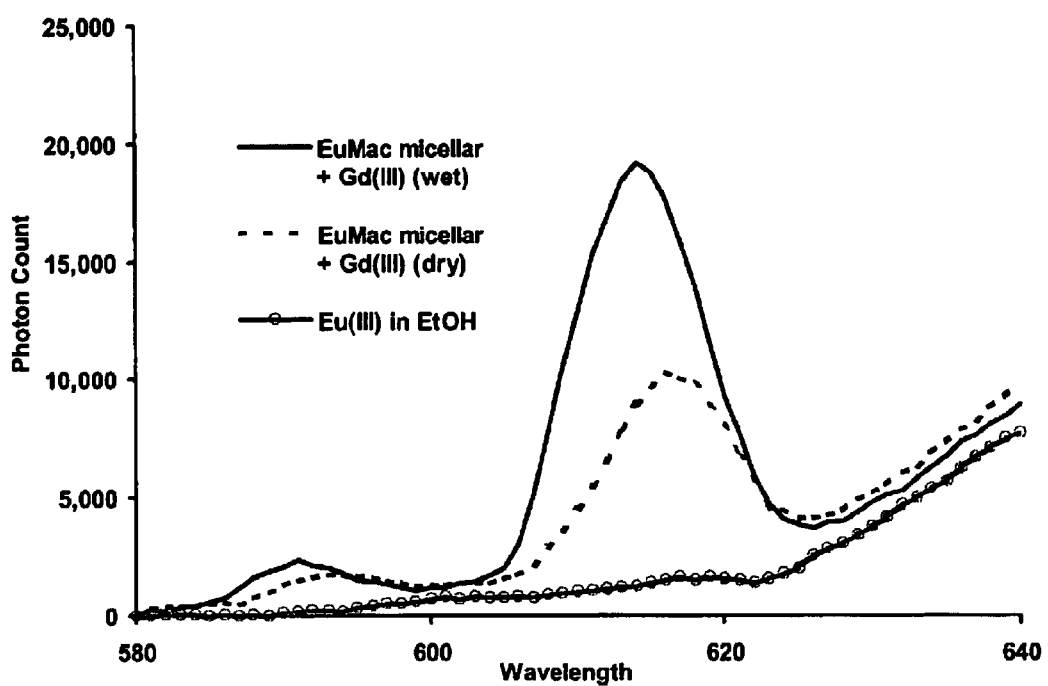
FIG. 4 is a graphical presentation of three emission spectra in the range from 580 to 640 nm.

Solid-State Studies of the Luminescence Intensity of EuMac in Gd-Containing Optimized Cofluorescence Solutions A. Procedure A strip of electrophoresis film (Sepraphore III, Gelman Sciences) was spotted with 0.010 mL of the Gd-containing, cofluorescence-optimized aqueous micellar solution of EuMac ($2.3 \times 10^{-7}$ M) of EXAMPLE I. The outline of the wet spot was marked in pencil to determine the area and its emission spectrum was recorded by reflectance. The strip was allowed to dry at room temperature, and the spectrum of the dry spot was measured again. The results of this experiment, illustrated in FIG. 4, showed that the cofluorescence effect for the EuMac, once established in micellar solution, is maintained in solid samples. Under the conditions described here, the EuMac was easily detected at a surface density of ca. $10^{-12}$ moles/cm$^2$ (FIG. 4). A second strip was similarly spotted with 0.010 mL of an ethanol solution of EuCl$_3$ ($2.3 \times 10^{-7}$ M) containing only the diketone HTTFA ($8.0 \times 10^{-4}$ M). The spectrum of the spot was recorded before the solvent had evaporated; the emission intensity was found to be much lower than that obtained from the aqueous cofluorescence solution containing the EuMac (FIG. 4); no luminescence was detected from this strip when dry.

FIG. 4 shows reflectance emission spectra (Excitation: 375 nm) of wet and dry spots obtained from a cofluorescence-optimized aqueous micellar solution of [Eu-macrocycle(acetate)$_2$](acetate) ($2.3 \times 10^{-7}$ M), and of a wet spot from an ethanol solution of Eu(III) ($2.3 \times 10^{-7}$ M) with only HTTFA added. Spectra were recorded under identical instrumental settings and the background from the paper was subtracted; however, the reflectance behavior of the paper changes upon drying. The rise in the curve above 630 nm is due to scattering from the paper.

EXAMPLE V

Enhancement of the Luminescence of the EuMac Complex by Yttrium(III) in Aqueous Micellar Solutions.

A. Materials.

(a) Yttrium trichloride, $1 \times 10^{-3}$ M, prepared from yttrium (III) oxide (99.999%, REO), commercially available from Alfa Aesar, catalog No. 11182 (1999–2000). The oxide, Y$_2$O$_3$ ($5.00 \times 10^{-4}$ mol), was dissolved in a minimal volume of 15% hydrochloric acid with mild heating. The resulting solution was evaporated to dryness under reduced pressure, and the white crystalline product thus obtained was dissolved in water to a total volume of 100 mL.

All other materials are the same as those listed in EXAMPLE I.

B. Procedure.

The luminescence enhancing experiments described in EXAMPLE I for Gd(III) were repeated using the chloride of Y(III) as the energy transfer donor. Y(III) caused a significant increase in the luminescence of the EuMac, when present in the optimized-cofluorescence matrix containing YCl$_3$ ($1.2 \times 10^{-4}$ M) instead of GdCl$_3$, as illustrated in FIG. 5.

Figure 5:
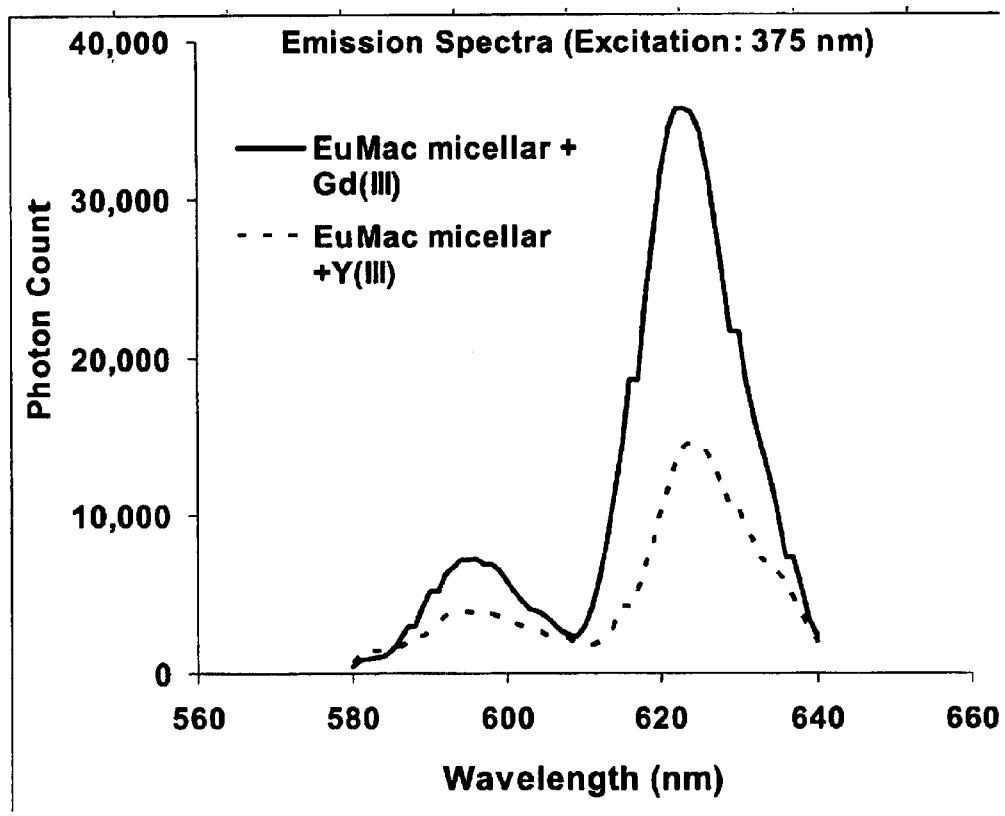
FIG. 5 is a graphical presentation of two emission spectra in the range from 560 to 660 nm.

FIG. 5 shows emission spectra (Excitation: 375 nm) of [Eu-macrocycle(acetate)$_2$](acetate) in two cofluorescence solutions, one containing Gd(III) and the other containing Y(III) as the energy transfer donor. (All other reagents are present at the same concentrations, see Table 1). The Gd(III) provides significantly stronger, 2.6 fold, enhancement relative to Y(III).

EXAMPLE VI

Enhancement of the Luminescence of the EuMac Complex by Lanthanum(III) in Aqueous Micellar Solutions.

A. Materials (a) Lanthanum trichloride, $1 \times 10^{-3}$ M, prepared from lanthanum(ill) oxide (99.999%, REO), commercially available from Alfa Aesar, catalog No. 11265 (1999–2000). The oxide, La$_2$O$_3$ ($5.00 \times 10^{-4}$ mol), was dissolved in a minimal volume of 15% hydrochloric acid with mild heating. The resulting solution was evaporated to dryness under reduced pressure, and the white crystalline product thus obtained was dissolved in water to a total volume of 100 mL.

All other materials are the same as those listed in EXAMPLE I.

B. Procedure

The procedures of EXAMPLE V were repeated with the substitution of lanthanium(III) chloride for yttrium(III) chloride. The luminescence enhancement produced by lanthanium(III) chloride was even lower than that produced by yttrium(III) chloride. Furthermore, the La(III) chloride used for these experiments, even though obtained from the purest commercially available oxide, still presented the problem of Eu(III) contamination previously discussed for gadolinium.

EXAMPLE VII

Luminescence Study of a Eu-Macrocycle-Avidin Conjugate, Using Gd(III) as Energy Transfer Donor in a Cofluorescence Solution A. Materials (a) EuMac-di-NCS, prepared according to U.S. Pat. No. 5,696,240 EXAMPLE XXIX B, step 1.

(b) Hexamethylenetetramine, ACS Reagent (HMTA), commercially available from Aldrich Chemical Co., Catalog No. 39,861-0 (1996–97), 10% aqueous solution adjusted to pH 7.6 with hydrochloric acid (HMTA pH 7.6).

Other materials were the same as those described in EXAMPLE I.

B. Procedure

1. Conjugation of EuMac-di-NCS with Avidin.

The Eu-Macrocycle-Avidin conjugate was prepared according to the procedures of U.S. Pat. No. 5,696,240 EXAMPLE XXIX B, step 2, with the substitution of the HMTA pH 7.6 buffer for the tricine buffer (0.10 M, pH=7.4).

2. Luminescence Study of the EuMac-Avidin Conjugate

Figure 6:
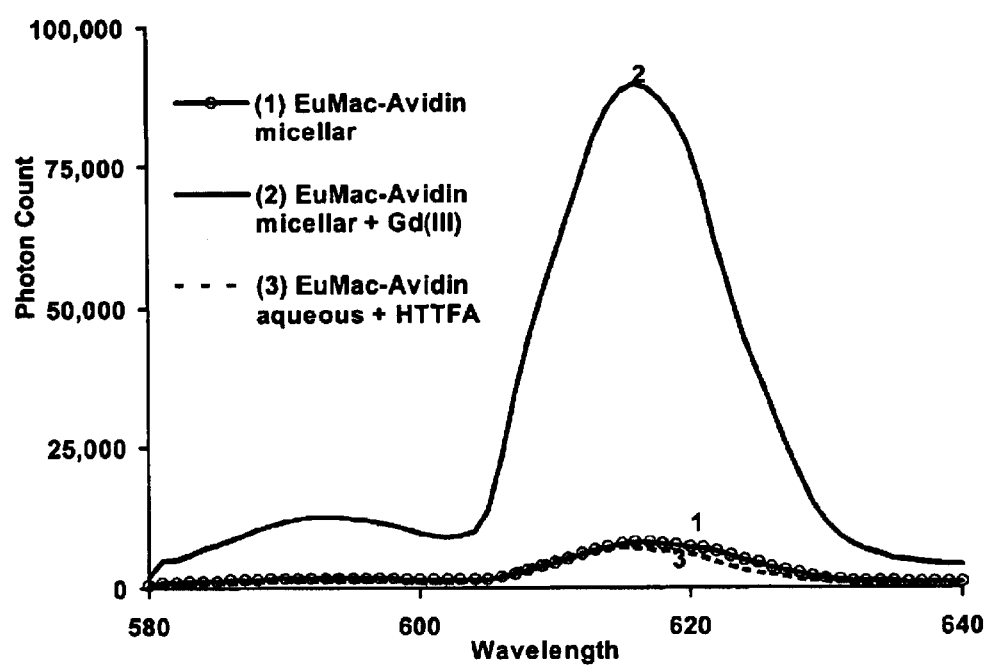
FIG. 6 is a graphical presentation of three emission spectra in the range from 580 to 640 nm.

The luminescence of the EuMac-Avidin conjugate described in Section 1 was studied by a protocol similar to that described in EXAMPLE I for the prototype EuMac complex. Specifically, one portion of the EuMac-Avidin was used to make a micellar solution containing Gd(III) in the optimized-cofluorescence matrix. (All components of this solution had the concentrations given in Table 1 except the europium of the EuMac-Avidin, which was present at $2.2 \times 10^{-6}$ mol/L as determined by atomic absorbtion analysis.) Another portion of EuMac-Avidin was used to make an identical micellar solution, except that Gd(III) was omitted. A third portion was used to make an aqueous solution containing only HTTFA. The emission spectra of the three solutions are shown in FIG. 6. At the same concentration, the maximum emission intensity of the EuMac-Avidin in the optimized micellar solution containing Gd(III) was more than ten times higher than that of the other solutions.

FIG. 6 shows emission spectra (Excitation: 365 nm) of the EuMac-Avidin at a concentration of $2.2 \times 10^{-6}$ mol europium)/L in: (1) A cofluorescence-optimized aqueous micellar solution. (2) Identical to the preceding solution but with Gd(III) chloride ($1.2 \times 10^{-4}$ M). (3) An aqueous buffered solution with only HTTFA added.

EXAMPLE VIII

Luminescence Study of a Eu-Macrocycle-Avidin Conjugate Attached to Agarose Beads, Using Gd (III) as Energy Transfer Donor A. Procedure 1. Preparation of Biotinylated Agarose Beads with Bound Eu-Mac-Avidin The EuMac-Avidin/biotinylated beads were prepared from the EuMac-Avidin of EXAMPLE VII and biotinylated agarose beads according to the procedures of U.S. Pat. No. 5,696,240 EXAMPLE XXIX B step 3.

2. Solid State Luminescence of Biotinylated Agarose Beads with Bound EuMac-Avidin The biotinylated agarose beads with bound EuMac-Avidin were tested as follows: (1) One portion of beads was treated with the optimized cofluorescence matrix containing no Gd(III); these beads showed no luminescence upon irradiation at 360 nm. (2) Another portion of beads was treated with the optimized cofluorescence matrix containing $1.2 \times 10^{-4}$ mol/L of Gd(III). These beads immediately displayed strong luminescence upon irradiation at 360 nm; the intensity remained unchanged for over one week when the beads were stored in the mother liquor in a refrigerator. The beads were then centrifuged, the supernatant was removed, and the beads were allowed to dry in air at room temperature. The dry beads still showed strong luminescence. (3) A third portion of beads was similarly treated with the Gd(III) optimized cofluorescence solution; the glowing beads were centrifuged and the supernatant was removed. A solution of HTTFA in ethanol was then added. The previously strong luminescence nearly disappeared.

EXAMPLE IX

Luminescence Study of a Eu-Macrocycle-Antibody Conjugate Attached to Apoptotic Cells, Using Gd (III) as Energy Transfer Donor A. Materials (a) Phoenix Flow Systems APO-BRDU™ Kit, part number AU1001.

(b) EuMac-mono-NCS is synthesized according to the procedures of Examples XI and XXXVI B Step 1 of U.S. Pat. No. 5,696,240 labeled PRB-1 (anti5BrdU).

(c) Hexamethylenetetramine, ACS Reagent (HMTA), commercially available from Aldrich Chemical Co., Catalog No. 39,861-0 (1996–97), 10% aqueous solution adjusted to pH 7.6 with hydrochloric acid (HMTA pH 7.6).

B. Procedure

1. Conjugation of the EuMac-Mono-NCS with the M607109 Monoclonal Antibody.

The derivatization, or conjugation, of the EuMac-mono-NCS with the M607109 monoclonal antibody is achieved by the procedures described in Example XXX Step 2 of U.S. Pat. No. 5,696,240 with the replacement of avidin by M607109 monoclonal anti-body. The europium-labeled M607109 is passed through 0.2-mm pore size membrane filters, and stored at 4° C. until use.

2. Suspension Staining of BrdU Containing Cells with EuMac-Antibody and DAPI.

(a) The positive control cells of the APO-BRDU™ Kit are resuspended by swirling the vials. A one mL aliquot of the control cell suspensions (approximately $1 \times 10^6$ cells) is removed and placed in 12×75 mm flow cytometry centrifuge tubes. The cell suspension is centrifuged (300 ×g) for 5 minutes and the 70% (v/v) ethanol supernatant is remove by aspiration, being careful to not disturb the cell pellet.

(b) The positive control cells are resuspended in 1 mL of HMTA pH 7.6 Buffer. The cells are centrifuged as before and the supernatant removed by aspiration.

(c) The resuspention in HMTA pH 7.6 buffer and centrifugation of step 2 are repeated.

(d) The antibody labeling solution is prepared by combining 5.00 microliters of EuMac-PRB-1 with 95.00 microliters of the HMTA pH 7.6 buffer.

(e) The positive control cell pellets are resuspended in 0.1 mL of the antibody labeling solution, the centrifuge tube is wrapped with aluminum foil, and the cells are incubated in the dark for 30 minutes at room temperature.

(f) 0.9 mL of a 2 micromolar DAPI solution in is added to the tube containing the cells suspended in the 0.1 mL of antibody labeling solution. The cells are incubated in the dark for a further 30 minutes at room temperature.

3. Centrifugal Cytology and Fluorescence Microscopy of the Dual Stained Cells.

(a) The 1 mL of dual stained cells is decanted into a Leif Centrifugal Cytology Bucket, which is centrifuged at 300× g for ten minutes at room temperature. The cells are sedimented onto and bound to an aminosilane treated slide (Labscientific, Inc. Livingston, N.Y.)

(b) The supernatant is removed by aspiration from the Centrifugal Cytology Bucket sample block and 0.2 mL of the cofluorescence solution of EXAMPLE I is added to the fixative chamber of the Centrifugal Cytology Bucket sample block.

(c) The Centrifugal Cytology Bucket is centrifuged at (300× g) for five minutes at room temperature, the sample block is separated from the slide, and a cover-glass is placed over the dispersion of fixed, stained cells.

(d) The cells are then viewed with a fluorescence microscope under episcopic illumination with mercury arc excitation. The excitation filter passes 365 nm light, which is reflected by a 400 nm dichroic mirror and excites the europium macrocycle. The emitted red light passes through the dichroic mirror and 618 nm narrow bandpass filter. The EuMac~PRB-1 bound to the incorporated 5BrdU is then observed or measured. The DAPI stained DNA in the nucleus is observed or measured through a broad-band emission 450 nm filter. DNA.

EXAMPLE X

Luminescence Study of a Eu-Macrocycle-Antibody Conjugate with Control (Non-apoptotic) Cells, Using Gd(III) as Energy Transfer Donor C. Procedure The procedure of EXAMPLE IX is repeated with the negative control cells of the APO-BRDU™ Kit. Surprisingly, there is no background binding of the EuMac~PRB-1.The $1.20 \times 10^{-4}$ M. Gd(III) cation blocks the nonspecific binding of the positively charged EuMac.

EXAMPLE XI

Measurement of Human Follicle Stimulating Hormone

The Time-Resolved Immunofluorometric Assay procedure of Madersbacher et al. Clin. Chem 39, pp. 1435–1439 (1993) is modified to; 1) replace the use of an expensive Time-Resolved fluorescence instrument by a conventional laboratory fluorometer, 2) replace the acid enhancement solution by the optimized Gd-cofluorescence solution of EXAMPLE I, and 3) read the sample in the dry state.

A. Materials (a) EuMac-mono-NCS is synthesized according to the procedures of Examples XI and XXXVI B Step 1 of U.S. Pat. No. 5,696,240 labeled PRB-1 (anti5BrdU).

(b) A monoclonal antibody, M94167, specific for the β-subunit of human FSH, commercially available from Fitzgerald Industries International, Inc., Catalog #: 10-F25, 1999.

(c) A monoclonal antibody, M607109, that recognizes a compatible epitope on human-FSH not located on the β-subunit of human FSH, commercially available from Fitzgerald Industries International, Inc., Catalog #: 10-F15, 1999.

(d) Follicle Stimulating Hormone (hFSH) (intact) human, commercially available from Fitzgerald Industries International, Inc., Catalog # 30-AF25, 1999.

(e) Washing Buffer: In a 1 L volumetric flask, the following are added: 7 g of hexamethylenetetramine, ACS Reagent (HMTA), commercially available from Aldrich Chemical Co., Catalog No. 39,861-0 (1996–97), 9 g of sodium chloride, 0.5 mL of Tween 20, commercially available from Aldrich Chemical Co., Catalog No. 27,434-8 (1998–1999) and 900 mL of water. The solution is adjusted to pH 7.75 with hydrochloric acid and water is added to bring the volume to 1L.

(f) Assay Buffer: In a 1 L volumetric flask, the following are added: 7 g of hexamethylenetetramine, ACS Reagent (HMTA), commercially available from Aldrich Chemical Co., Catalog No. 39,861-0 (1996–97), 9 g of sodium chloride, 5 g of bovine serum albumin, commercially available from Sigma Biochemicals and Reagents for Life Science Research, Catalog No. B 4267 (1999), 0.5 g of bovine IgG commercially available from Sigma Biochemicals and Reagents for Life Science Research, Catalog No. I 5506 (1999), 0.1 g Tween 40, commercially available from Aldrich Chemical Co., Catalog No. 27,435-6 (1996–97), and 900 mL of water. The solution is adjusted to pH 7.75 with hydrochloric acid and water is added to bring to volume to 1 L.

B. Procedure (a) The derivatization, or conjugation, of the EuMac-mono-NCS with the M607109 monoclonal antibody is achieved by the procedures described in Example XXX Step 2 of U.S. Pat. No. 5,696,240 with the replacement of avidin by M607109 monoclonal antibody. The europium-labeled M607109 is passed through 0.2-mm pore size membrane filters, and stored at 4° C. until use.

(b) Polystyrene microtiter strips (Immuno Module Maxisorp; Nalge Nunc International) are coated overnight, at 4° C., with 2 micrograms of the M94167 monoclonal antibody in 100 microliters of PBS per well. Subsequently, the strips are incubated for 45 min at 37° C. with 200 mL of PBS containing bovine serum albumin (10 g/L) and then washed four times with the washing buffer.

(c) Graded amounts of the antigen (hFSH) in 100 microliters of Assay Buffer are added to the MCA-coated wells and allowed to react on an orbit shaker at 500 rpm for 90 min at 22° C.

(d) Twenty-five ng of europium-labeled M607109 in 100 microliters of assay buffer is added to each well and the strips are incubated for 30 min at 22° C. on an orbit shaker (500 rpm).

(e) The plates are washed six times with the washing buffer.

(f) One hundred microliters of the optimized-cofluorescence matrix are added to each well. All components of this solution, except europium, have the concentrations given in Table 1. The optimized-cofluorescence matrix is allowed to react with the intact europium-labeled M607109 for 10 min on an orbit shaker (500 rpm).

(g) The wells are air dried and the bottoms are cut-out (h) The fluorescence is measured for 5 s in a SLM-8000 fluorometer with the emission monochromator set at 618 nm and emission slit adjusted to have a 10 nm band width at half maximum. The excitation is at 365 nm with a 16 nm band width at half maximum.

(i) The signal to noise ratio at 8 ng/L of FSH is higher than 1,000 and the maximum concentration measurable by the SLM-8000 exceeds 10,000 ng/L. Thus, the performance of the system described here is better than immunoenzymetric and immunoradiometric assays even though it is slightly inferior to time-resolved immunofluorescence assays. The system described here also has the significant advantage of employing conventional instrumentation that includes very inexpensive light sources and detectors and is therefore suited for bedside use and for field assays employing dipsticks.

EXAMPLE XII

Time-Gated Measurement of Human Follicle Stimulating Hormone

A. Procedure

The procedures of EXAMPLE XI are repeated through step (f). Time-resolved fluorescence is measured for 1 s in a time-gated fluorometer (Arcus 1230, Wallac, Finland). Thus, the performance of the system described here is better than immunoenzymetric and immunoradiometric assays even though it is slightly inferior to that of the DELFIA reagents which are optimized for the Arcus 1230. However, the luminescence is localized to the antigen. Thus, more complex systems, such as arrays of different antigens, can be measured because the luminescing species remains attached to the antigen. Background luminescence from the solution can be minimized and signal maximized by employing optics with a narrow depth of focus and low F number.

EXAMPLE XIII

A Competitive Immunological Determination of Insulin

A. Materials:

EuMac labelled insulin (EuMac-Insulin) is achieved by the procedures described in EXAMPLE XXIX of U.S. Pat. No. 5,696,240 with the substitution of insulin for the avidin and the substitution of the EuMac-mono-NCS of the procedures of U.S. Pat. No. 5,696,240 Example XXXVI B Step 1 for the EuMac-di-NCS.

(a) Insulin (commercially available from Sigma Biochemicals and Reagents for Life Science Research, Catalog No. 10259. 1999).

(b) A monoclonal antibody against human insulin (anti-insulin) commercially available from Fitzgerald Industries International, Inc., Catalogue #: 10–130, 1999.

(c) The Washing Buffer of EXAMPLE XI.

(d) The Assay Buffer of EXAMPLE XI

B. Procedure:

(a) Polystyrene microtiter strips (Immuno Module Maxisorp; Nalge Nunc International) are coated overnight, at 4° C., with 2 micrograms of the anti-insulin monoclonal antibody in 100 microliters of PBS per well. Subsequently, the strips are incubated for 45 min at 37° C. with 200 mL of PBS containing bovine serum albumin (10 g/L) and then washed four times with the washing buffer.

(b) Ten microliters EuMac-Insulin (20 ng) and 10 uL insulin standard (0, 10, 50, 200,1000 and 10000 ng) in 100 microliters of Assay Buffer are added to the monoclonal antibody coated wells and allowed to react on an orbit shaker at 500 rpm for 90 min at 22° C.

(c) The plates are washed six times with the washing buffer.

(d) One hundred microliters of the optimized-cofluorescence matrix are added to each well. All components of this solution, except europium, have the concentrations given in Table 1. The optimized-cofluorescence matrix is allowed to react with the EuMac-Insulin for 10 min on an orbit shaker (500 rpm).

(e) The wells are air dried and the bottoms are cut-out.

(f) The fluorescence is measured for 5 s in a SLM-8000 fluorometer with the emission monochromator set at 618 nm and emission slit adjusted to have a 10 nm band width at half maximum. The excitation is at 365 nm with a 16 nm band width at half maximum.

(g) Whereafter the fluorescence for each sample was measured. According to the competitive determination principle, the fluorescence intensity of the sample decreases, as the amount of "cold" insulin increases.

In contrast to the examples given in Soini et al., U.S. Pat. No. 4,587,233 Method for Quantitative Determination of a Biospecific affinity Reaction, (1986) U.S. Pat. No. 4,587,233 and the description of similar uses of rare-earth luminescent tags in I. Hemmila et al.(1994) Bioanalytical applications of labelling technologies, A review of trends and new opportunities in biospecific assay, based on the product offering of Wallac, an EG&G company, Edited by I. Hemmila et al. ISBN 951-9489-32-0. the analyte can be measured in a conventional fluorometer without the destruction and formation of the complex. Since the emitting species is bound to a solid surface, the depth of focus can be minimized which in turn minimizes background noise from the solution.

EXAMPLE XIV

Time-Gated Measurement of Insulin

A. Procedure

The procedures of EXAMPLE XIII are repeated through step 6. Time-resolved fluorescence was measured for 1 s in a time-gated fluorometer (Arcus 1230, Wallac, Finland). The results are similar to those of EXAMPLE XIII.

EXAMPLE XV

Enhancement of the Luminescence of the SmMac Complex by Gadolinium(III) in Aqueous Micellar Solutions.

A. Materials (a) [Sm-macrocycle(acetate)$_2$](acetate), prepared as previously by De Cola et al. Inorganic Chemistry Vol. 25, 1729–1732 (1986), $1.0 \times 10^{-3}$ M stock solution in anhydrous ethanol. This solution served as primary stock from which more dilute stock solutions were made as necessary.

All other materials were the same as those used in EXAMPLE I.

B. Procedure

A set of Gd-containing cofluorescence solutions having decreasing SmMac concentrations ($1.0 \times 10^{-5}$ M, $1.0 \times 10^{-6}$ M, $1.0 \times 10^{-7}$ M, $1.0 \times 10^{-8}$ M, $5.0 \times 10^{-9}$ M) were prepared from the SmMac stock solution, following a protocol similar to that described for EuMac in EXAMPLE I, except that a precofluorescence solution containing buffer, detergent, and phenanthroline was first made.

The SmMac complex exhibited the highest luminescence intensity in a Gd-containing cofluorescence solution in which the diketone was 1,1,1-trifluoro-4(2-thienyl)-2,4-butanedione (HTTFA), and all components of the final solution, with the exception of SmMac, had the concentrations given in Table 1.

For comparison, a cofluorescence solution of SmMac ($1.0 \times 10^{-5}$ M) containing all components at the concentrations of Table 1, but no gadolinium, was also prepared.

Figure 7:
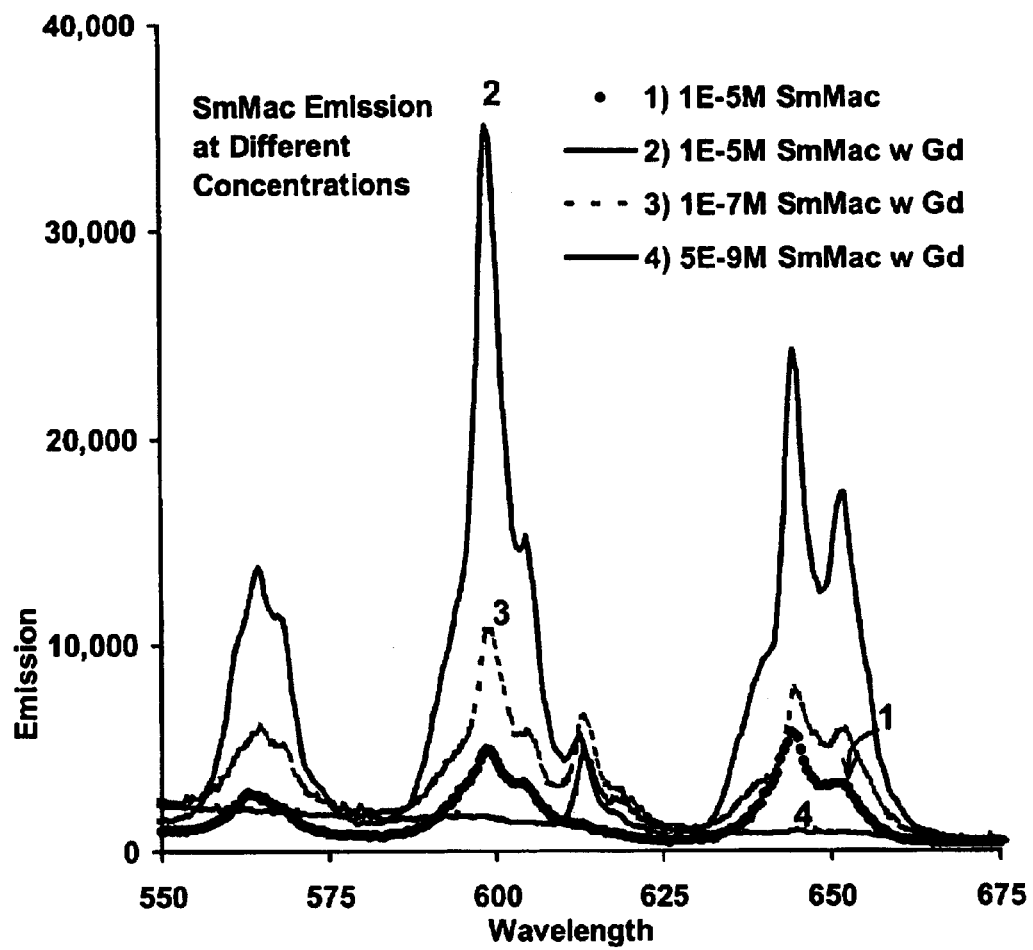
FIG. 7 is a graphical presentation of four emission spectra in the range from 550 to 675 nm.

The emission spectra of all solutions were obtained as described in EXAMPLE I, except that the SPEX 1692T spectrofluorometer was used. The results are illustrated in FIG. 7. It should be pointed out that the problem of Eu(III) contamination in the gadolinium used for as energy transfer donor, discussed in EXAMPLE II for EuMac, also affects the SmMac spectra in the lowest concentration range.

FIG. 7 shows emission spectra (excitation, 367 nm) of [Sm-macrocycle(acetate)$_2$](acetate) at three different concentrations, $1 \times 10^{-5}$ M, $1 \times 10^{-7}$ M, $1 \times 10^{-9}$ M, in cofluorescence-optimized solutions with and without Gd(III). The solutions that contain gadolinium also contain "free" Eu(III) (approximately $4 \times 10^{-11}$ M) as contaminant. The SmMac spectrum shows three emissions at {563}, {599}, and {644} nm, arising from the $^4G_{5/2} \to {}^6H_{5/2}$, $^4G_{5/2} \to {}^6H_{7/2}$, and $^4G_{5/2} \to {}^6H_{9/2}$ transitions of Sm(III); the constant-intensity emission at 614 nm arises from the $^5D_0 \to {}^7F_2$ transition of the Eu(III) contaminant.

EXAMPLE XVI

Comparison of the Luminescence Intensity of the SmMac Complex in a Gd-Containing Cofluorescence Solution and in Ethanol Solutions with Diketone Enhancers A. Materials.

(a) [Sm-macrocycle(acetate)$_2$](acetate), prepared as previously by De Cola et al. Inorganic Chemistry Vol. 25,1729–1732 (1986), $1.0 \times 10^{-3}$ M stock solution in anhydrous ethanol. This solution served as primary stock from which more dilute stock solutions were made as necessary.

All materials were the same as those used in EXAMPLE XV.

B. Procedure

The following solutions were prepared: (a) a Gd-containing cofluorescence solution of SmMac ($1.0 \times 10^{-4}$ M) following the protocol of EXAMPLE I, (b) a solution of SmMac ($1.0 \times 10^{-4}$ M) in anhydrous ethanol, containing 1,1,1-trifluoro-4(2-thienyl)-2,4-butanedione (HTTFA, $4.0 \times 10^{-4}$ M), (c) a solution of SmMac ($10 \times 10^{-4}$ M) in anhydrous ethanol, containing 1,1,1-trifluoro-4(2-naphtyl)-2,4-butanedione (HTFNA, $4.0 \times 10^{-4}$ M). The luminescence spectra of the solutions were obtained as described in EXAMPLE II, using the SPEX 1692T spectrofluorometer. The results are illustrated in FIG. 8 and FIG. 9.

Figure 8:
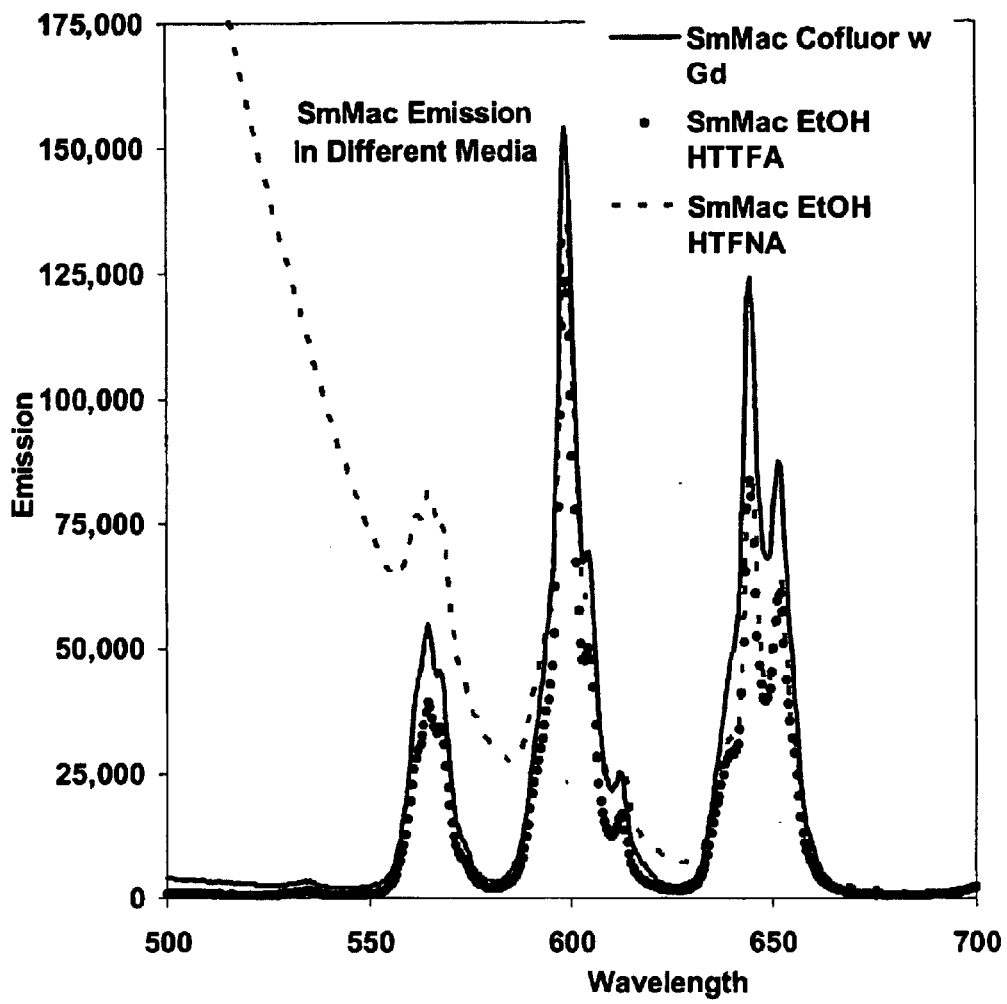
FIG. 8 is a graphical presentation of three emission spectra in the range from 500 to 700 nm.
Figure 9:
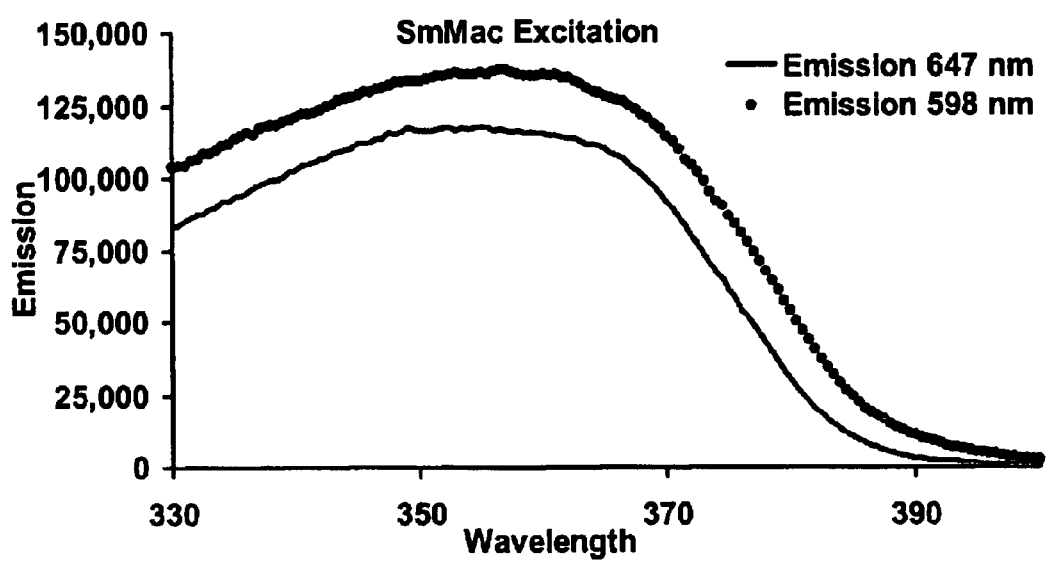
FIG. 9 is a graphical presentation of two excitation spectra in the range from 330 to 390 nm.

FIG. 8 shows emission spectra (excitation, 367 nm) of [Sm-macrocycle(acetate)$_2$](acetate) ($1.0 \times 10^{-4}$ M) in: (a) a Gd-containing optimized cofluorescence solution, (b) an ethanol solution containing HTTFA ($4.0 \times 10^{-4}$ M), and (c) an ethanol solution containing HTFNA ($4.0 \times 10^{-4}$ M). The emission of the three solutions have the same shape in the region of 550 to 650 nanometers and thus are the result of the same electronic transitions FIG. 9 shows excitation spectra of [Sm-macrocycle (acetate)$_2$](acetate) ($1.0 \times 10^{-4}$ M) in an ethanol solution containing HTTFA ($4.0 \times 10^{-4}$ M), for emission of 598.5 and 647.0 nm, respectively. The shapes of the excitation spectra including their maxima for the two emissions are identical.

EXAMPLE XVII

Luminescence Study of a Sm-Macrocycle-Avidin Conjugate, Using Gd(III) as Energy Transfer Donor A. Materials (a) A samarium(III) macrocyclic complex with two 4-isothiocyanatobenzyl peripheral groups, SmMac-di-NCS, is prepared as previously described for the europium analog according to the procedures of U.S. Pat. No. 5,696,240 EXAMPLE XI and EXAMPLE XXIX B step 1, with the substitution of samarium for europium.

(b) All other materials are the same as those used in the procedures of U.S. Pat. No. 5,696,240 Example XXXVI B Step 1.

B. Procedure

The conjugation of the SmMac-di-NCS complex to avidin, the chromatographic purification of the SmMac-avidin conjugate, and the luminescence study of the latter, are carried out according to the procedures described in U.S. Pat. No. 5,696,240 Example XXXVI B Step 1 for the europium analog were employed to synthesize the SmMac-mono-NCS. The procedures described in U.S. Pat. No. 5,696,240 Example XXIX Step 2 were employed for the conjugation with avidin. Similar to the EuMac-avidin conjugate, the SmMac-Avidin conjugate shows intense luminescence when present in a Gd-containing optimized cofluorescence solution in which the buffer, detergent, diketone, and synergistic ligands all have the concentrations listed in Table 1.

EXAMPLE XVIII

Coupling of The Hexa-aza-macrocyclic Complex of Samarium(Ill) Acetate Having a Pendant (4-isothiocyanatophenyl)methyl Group to an Antibody Via Thiourea Linkages A. Materials (a) A samarium(III) macrocyclic complex having a pendant isothiocyanate group, SmMac-mono-NCS, is prepared as previously described for the europium analog in the procedures of U.S. Pat. No. 5,696,240 Example XXXVI B Step 1 with the substitution of samarium for europium.

(b) PRB-1, an antibody specific for 5BrdU marker for DNA, available from Phoenix Flow Systems, San Diego, Calif.

All other materials are the same as those listed in U.S. Pat. No. 5,696,240 Example XXIX B. Procedure The SmMac-mono-NCS is complex is coupled to PRB-1 anti5BrdU by the procedures of U.S. Pat. No. 5,696,240 Example XXIX with the substitution of the SmMac-mono-NCS for the EuMac-di-NCS and PRB-1 for avidin.

EXAMPLE XIX

Simultaneous Enhancement of the Luminescence of a EuMac and a SmMac Complex by Gadolinium (III) in Aqueous Micellar Solutions.

In this example, the simultaneous detection of europium and samarium macrocycles has been demonstrated.

A. Materials (a) The EuMac of EXAMPLE I.

(b) The SmMac of EXAMPLE XV.

All other materials were the same as those used in EXAMPLE I

B. Procedure (a) The following Gd-containing cofluorescence solution were prepared: (a) SmMac ($5.0 \times 10^{-6}$ M), (b) EuMac ($5.7 \times 10^{-8}$ M), (c) SmMac ($5.0 \times 10^{-6}$ M) and EuMac ($1.4 \times 10^{-7}$ M), (d) SmMac ($5.0 \times 10^{-6}$ M) and EuMac ($5.7 \times 10^{-8}$ M). The protocol for the preparation of these solution was the same as that described in EXAMPLE XV.

(b) The emission and excitation spectra were obtained with the SLM-8000 instrument as described in EXAMPLE I except the slits (both excitation and emission) were set as described below.

Figure 10:
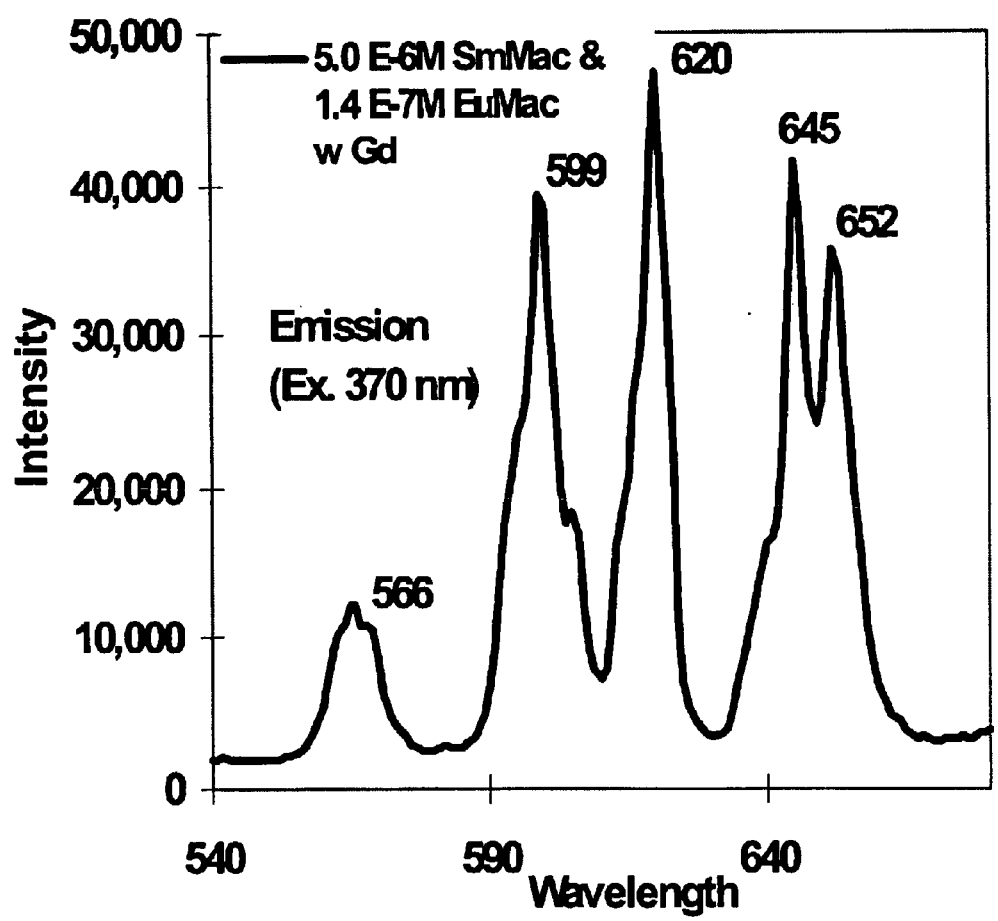
FIG. 10 is a graphical presentation of an emission spectrum in the range from 540 to 680 nm.
Figure 11:
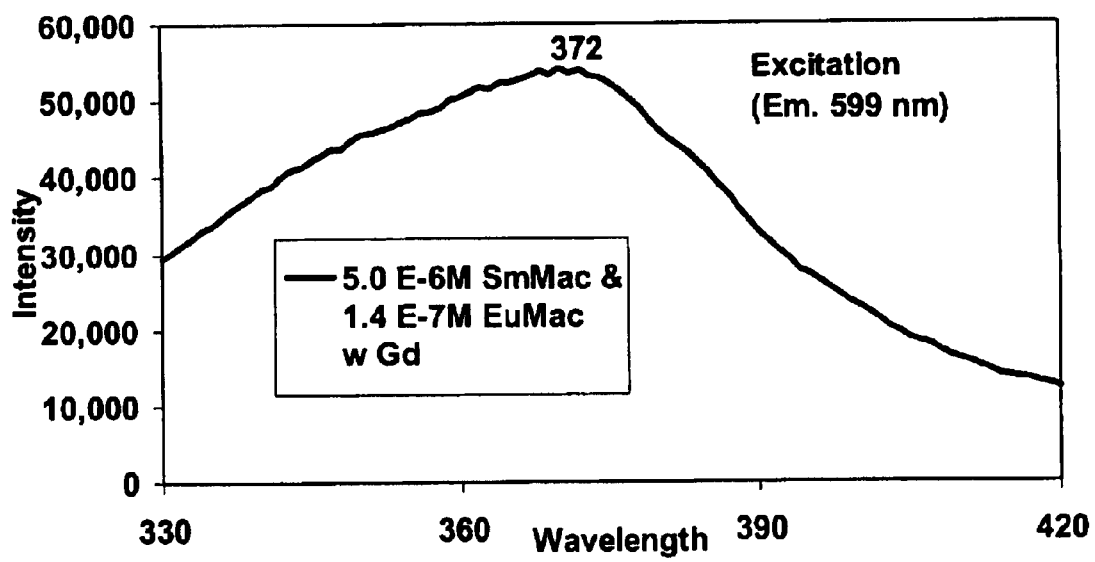
FIG. 11 is a graphical presentation of an excitation spectrum in the range from 330 to 420 nm.

The emission and excitation spectra of a Gd-containing cofluorescence solution prepared from a mixture of the EuMac ($1.4 \times 10^{-7}$ M) and SmMac ($5.0 \times 10^{-6}$ M) are shown respectively in FIG. 10 and FIG. 11.

FIG. 10 shows an emission spectrum (excitation, 370 nm) of a gadolinium-induced cofluorescence solution containing $5.0 \times 10^{-6}$ M [Sm-macrocycle(acetate)$_2$](acetate) and $1.4 \times 10^{-7}$ M [Eu-macrocycle(acetate)$_2$](acetate); all other components as in Table 1. The SmMac and EuMac complexes were combined prior to micelle formation and their concentrations were chosen to provide approximately equal emission intensities in the mixture. The $^5D_0 \rightarrow ^7F_2$ (619 nm) emission of the EuMac species is well separated from the neighboring $^4G_{5/2} \rightarrow ^6H_{7/2}$ (599 nm), and $^4G_{5/2} \rightarrow ^6H_{9/2}$ (644 and 652 nm) emissions of the SmMac, so that the intensities of each emission can be measured independently. The excitation and emission slits were respectively 16 and 2 nm. At this concentration ratio, the emissions of the EuMac and SmMac in the combined solution have very similar intensities.

FIG. 11 shows an Excitation spectrum of the SmMac complex (emission, 599 nm) in a gadolinium-induced cofluorescence solution containing $5.0 \times 10^{-6}$ M [Sm-macrocycle(acetate)$_2$](acetate) and $1.4 \times 10^{-7}$ M [Eu-macrocycle(acetate)$_2$](acetate). All other components had the concentrations given in Table 1 and the SmMac and EuMac were combined prior to micelle formation. The excitation and emission slits were 8 and 4 nm, respectively. The excitation spectrum of the EuMac complex is nearly identical.

Figure 12:
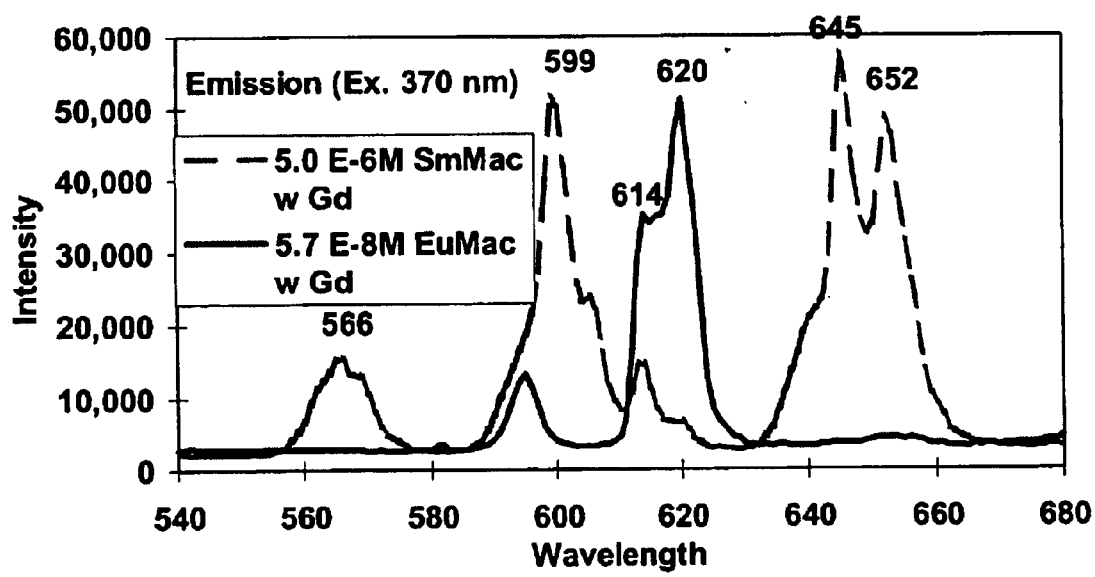
FIG. 12 is a graphical presentation of a composite of two emission spectra in the range from 540 to 680 nm.

FIG. 12 is a composite of the emission spectra (excitation, 370 nm) of two gadolinium-induced cofluorescence solutions, one containing SmMac ($5.0 \times 10^{-6}$ M) alone and the other containing EuMac ($5.7 \times 10^{-8}$ M) alone. The concentrations of the macrocyclic complexes were chosen to provide approximately equal emission intensities. The superimposed emission spectra of two Gd-containing cofluorescence solutions, one with EuMac alone ($1.4 \times 10^{-7}$ M) and the other with SmMac alone (5.0×10–6 M), are shown in FIG. 12; At this concentration ratio, the EuMac alone and the SmMac alone have very similar emission intensities.

The major peaks of FIG. 10 are also found in FIG. 12. Clearly the EuMac peak at 620 nm has very little overlap with the 599 nm peak of the SmMac and negligible overlap with the combined 645 and 652 nm of the SmMac. The peak at 614 nm is due to europium contamination as described in EXAMPLE II. These long wavelength emissions are clearly separable from those of conventional ultraviolet excited DNA dyes including DAPI.

Thus the use of two MMacs together or in conjunction with other dyes increases the number of measurable analytes and in the case of ultraviolet excited dyes simplifies the instrumentation required for excitation of the luminescence and/or fluorescence.

EXAMPLE XX

Simultaneous use of Lanthanide Tags as Secondary Reagents for Comparative Genomic Hybridization Measurements In this Example, methods of this invention to analyze genomes by Comparative Genomic Hybridization (CGH)

are exemplified by employing two luminescence species that are each attached to a secondary reagent. This procedure is based on U.S. Pat. No. 5,976,790. Pinkel et al. U.S. Pat. No. 5,976,790 describe the following steps for CGH:

1. Removal of Repetitive Sequences and/or Disabling the Hybridization Capacity of Repetitive Sequences.
2. Labeling the Nucleic Acid Fragments of the Subject Nucleic Acids.
3. In Situ Hybridization.

Pinkel et al. 1999 summarize In Situ Hybridization as: "Generally in situ hybridization comprises the following major steps: (1) fixation of tissue or biological structure to be examined, (2) prehybridization treatment of the biological structure to increase accessibility of target DNA, and to reduce nonspecific binding, (3) hybridization of the mixture of nucleic acids to the nucleic acid in the biological structure or tissue; (4) posthybridization washes to remove nucleic acid fragments not bound in the hybridization and (5) detection of the hybridized nucleic acid fragments."

They state that their present technique is limited: "At the current stage of development of CGH, sensitivity is primarily limited by the granularity of the hybridization signals in the metaphase chromosomes. Further improvements in sensitivity will be achieved by optimization of the probe concentration and labeling, and by the averaging of the green-to-red fluorescence ratios from several metaphase spreads."

A. Materials (a) The SmMac-Avidin Conjugate, prepared according to EXAMPLE XVII (b) The EuMac-anti-digoxigenin, prepared by the procedures described in Example XXX of U.S. Pat. No. 5,696,240 with the replacement of the avidin by anti-digoxigenin (SIGMA 1999 #D 8156).

(c) All other materials are as described in U.S. Pat. No. 5,976,790.

B. Procedure (a) The procedure of Kallioniemi et al. Proc. Natl. Acad. Sci. USA. 91, pp. 2156–2160 (1994) is followed. The target metaphase slides are prepared from phytohemagglutinin-stimulated peripheral blood lymphocytes from a normal male. To assess the hybridization characteristics, each batch of slides is extensively tested with labeled normal genomic DNA and with whole chromosome painting probes. If evidence of dim or non-uniform hybridization is detected, the entire batch of slides is abandoned, and another batch is prepared.

(b) A DNA sample from abnormal tissue is labeled with biotin-14dATP (test sample). A second DNA sample from normal tissue is labeled with digoxigenin-11-dUTP (normal reference DNA) using the Bionick labeling system (BRL).

(c) The amounts of DNase and DNA polymerase I are adjusted so that the probe-fragment-size distribution after labeling is 600–2000 base pairs (a smear in a nondenaturing agarose gel). Probe fragments of this size are necessary to obtain uniform, intense hybridization.

(d) Sixty to 100 ng of each of the labeled probes and 5 micrograms of unlabeled Cot-1 DNA are precipitated with ethanol.

(e) The DNAs are dissolved in 10 microliters of hybridization buffer [50% (vol/vol) formamide/10% (wt/vol) dextran sulfate/2× standard saline/citrate, pH 7], denatured at 70° C. for 5 min, and incubated at 37° C. for 30 min.

(f) Metaphase slides are denatured in 70% formamide/2× standard saline/citrate, pH 7 at 70° C. for 3 min, dehydrated in 70%, 85%, and 100% ethanol, treated with proteinase K (0.1 microgram/mL in 20 mM Tris/2 mM $CaCl_2$, pH 7.5) at 37° C. for 7.5 min, and dehydrated again.

(g) The hybridization mixture is applied on slides and hybridized for 2–3 days at 37° C. in a moist chamber.

(h) After hybridization, the slides are washed and stained by using a single layer of SmMac-Avidin Conjugate (to visualize bound biotinylated probes) at 5 micrograms/mL and EuMac-anti-digoxigenin at 1 microgram/mL (to visualize bound digoxigenin-labeled probes).

(i) Samples are counterstained with DAPI in an anti-fade solution.

(j) The slide is dipped in the Gd-containing cofluorescence solution of the protocol of EXAMPLE I and a coverslip is applied.

(k) A fluorescence microscope with episcopic illumination and equipped with a digitized camera is employed to image and measure the chromosomes. The excitation light is the 365 emission from mercury. This light is separated from the luminescence emission by a dichroic mirror that reflects half the light at 400 nm. A movable emission filter holder has at least 3 filters: a wide band 450 filter for DAPI, a narrow 618 nm filter for the Eu(III) emission, and a 599 and 644 nm filter for the Sm(III) emission. The band widths of the filters for the lanthanide(III) ions are 10 nm full-width at half maximum.

(l) The individual chromosomes are identified by the DAPI banding and their size. The signal to noise of both the Eu(III) and Sm(III) and lack of cross-talk between the two spectra increases the precision of the measurements permitting probe-fragments smaller than 600 base pairs to be used and eliminating the need for signal averaging from multiple chromosomes of the same type.

EXAMPLE XXI

Preparation of a Lanthanide-Labeled Nucleotide Triphosphate

A. Materials (a) 5-(3-Aminoallyl)-2'-deoxyuridine 5'-triphosphate Sodium Salt, commercially available from Sigma Chemical Co., Catalog No. A0410.

(b) Tricine, commercially available from Aldrich Chemical Co., Catalog No 16,378-3 (1998–1999), 0.1 M. adjusted with NaOH to pH 8.5 (Tricine-8.5).

(c) 0.1 M triethylamine, commercially available from Aldrich Chemical Co., Catalog No 47,128-3 (1998–1999), is bubbled with $CO_2$ to produce a pH 7.5 triethylamonium bicarbonate solution.

(d) 0.9 M triethylamine is bubbled with $CO_2$ to produce a pH 7.5 triethylamonium bicarbonate solution.

B. Procedure

The procedures of Ward et al. (1995) U.S. Pat. No. 5,449,767, EXAMPLE 1 and 2, c) are followed with the substitution of the EuMac-mono-NCS of EXAMPLE VII for Biotinyl-N-hydroxysuccinimide ester. The EuMac-mono-NCS (Formula VI) is coupled to 5-(3-Aminoallyl)-2'-deoxyuridine 5'-triphosphate (AA-dUTP) (Formula VII) to produce a (europium macrocycle)-labeled nucleoside, EuMac-5-deoxyuridine (Formula VIII).

AA-dUTP-$H_2O$ (63 mg, 0.1 mmole) is dissolved in 20 ml of Tricine-8.5, and EuMac-mono-NCS (34.1 mg, 0.1 mmole) dissolved in 2 ml of DMSO is added. The reaction mixture is left at room temperature for four hours and then is loaded directly onto a 30 ml column of DEAE-Sephadex TM A-25, preequilibrated with Tricine-7.5. The column is eluted with a 400 mL linear gradient (0.1–0.9 M) of triethylamonium bicarbonate. Fractions containing EuMac-5- deoxyuridine are desalted by rotary evaporation in the presence of methanol and redissolved in water. For long term storage, the conjugated nucleotide is converted to the sodium salt by briefly stirring the solution in the presence of Dowex™ 50 (Na$^+$ form). After the resin is removed by filtration, the nucleotide is precipitated by the addition of three volumes of cold ethanol, washed with ethyl ether, dried in vacuo over sodium hydroxide pellets, and stored in a desiccator at −20° C. For immediate use, the EuMac-5-deoxyuridine is dissolved in 20 mM Tris-HCl buffer at pH 7.5, to give a final nucleotide concentration of 5 mM. However, the conjugated nucleotide no longer reacts with ninhydrin, a characteristic reaction of the AA-dUTP and AA-UTP starting materials.

The procedure is repeated with the replacement of the europium(III) by samarium(III) to produce Sm-Mac-5-deoxyuridine.

(c) Hexamethylenetetramine, ACS Reagent (HMTA), commercially available from Aldrich Chemical Co., Catalog No. 39,861-0 (1996–97), 10% aqueous solution containing 0.1% NP40, commercially available from Sigma Biochemicals and Reagents for Life Science Research, Catalog No. 12708-87-0 (1999) is adjusted to pH 8.0 with hydrochloric acid (HMTA-NP40 pH 8.0).

B. Procedure

The procedure of Bastian et al. Cancer Research 58 pp. 2170–2175 (1998) is followed.

1. DNA Isolation (a) Twenty microns sections of previously frozen tumor containing tissue are cut on a cryostat, fixed in 70, 85. and 100% ethanol for 5 min each; and stored at 4° C. until microdissection. Every five sections, a 5 micron section is cut and stained with H&E to guide the microdissection.

(b) Microdissection is carried out manually under a dissecting microscope

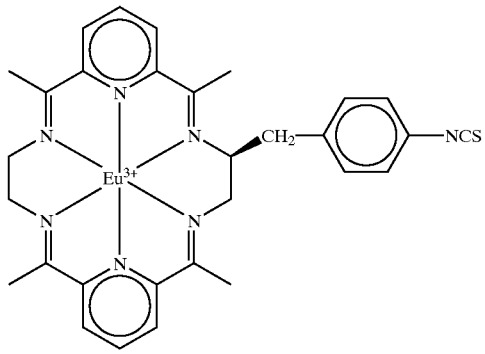

Formula VI

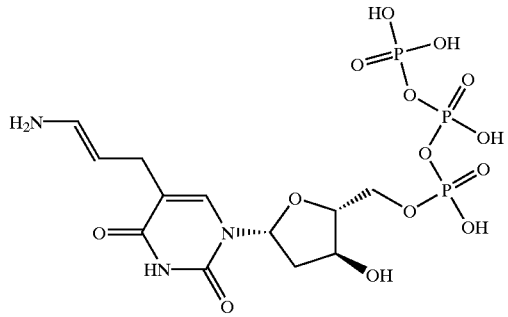

Formula VII

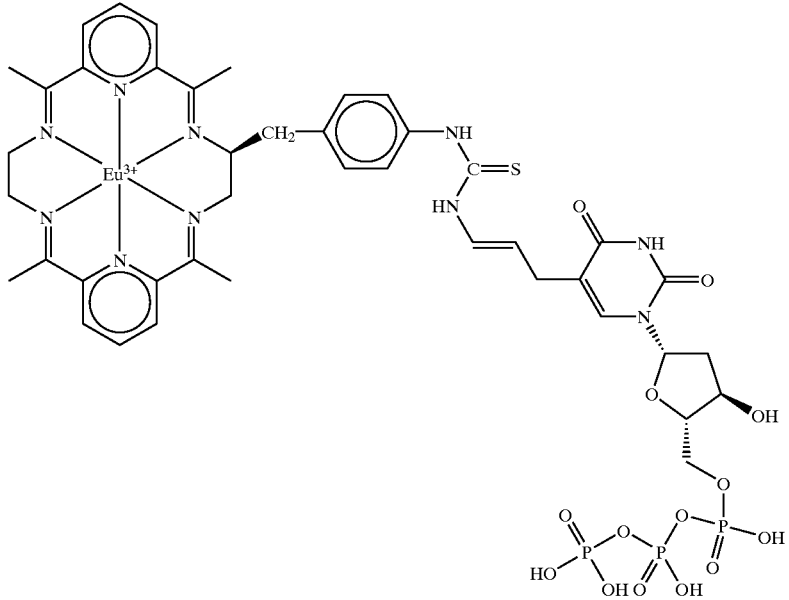

Formula VIII

EXAMPLE XXII

Simultaneous use of Lanthanide Tagged DNA for Comparative Genomic Hybridization

A. Materials (a) The EuMac-5-deoxyuridine (Formula VIII) of EXAMPLE XXI.

(b) The SmMac-5-deoxyuridine of EXAMPLE XXI.

(c) The previously frozen tissue is incubated until complete digestion (3–7 days) with proteinase K (Life Technologies. Inc., Gaithersburg. MD) in a buffer containing 50 mM Tris (pH 8.5), 1 mM EDTA, and 0.5% Tween 20.

(d) DNA is extracted with phenol-chloroform-isoamylalcohol (25: 24:1, v/v), precipitated with 7.5 M ammonium acetate and 100% ethanol, and resuspended in water. The amount of DNA obtained ranged from 3 to 50 micrograms.

2. Comparative Genomic Hybridization (a) The tumor DNA is labeled with EuMac-5dUTP and the reference DNA is labeled with SmMac-5dUTP (standard labeling) and with the labeling reversed. Labeling is performed by nick translation. The nick translation conditions are adjusted so that the maximal probe size after labeling ranged between 800 and 1500 base pairs.

(b) The hybridization mixture consists of 200 to 1000 ng of EuMac labeled tumor DNA, 200 to 2000 ng of SmMac labeled sex matched normal human reference DNA from peripheral blood lymphocytes and 25 micrograms of human Cot-1 DNA (Life Technologies, Inc.) dissolved in 10 microl of hybridization buffer [50% formamide, 10% dextran sulfate, and 2× SSC (pH 7.0)]. Hybridization is carried out for 2 or 3 days at 37° C. to normal metaphases (13). All samples are investigated with a single batch of metaphase slides.

(c) Slides are washed three times in a washing solution [50% formamide in 2× SSC (pH 7.0)] at 45° C., once in HMTA-NP40 pH 8.0, and once in distilled water (both washes are for 10 min at room temperature).

(d) Slides are counterstained with 4', 6-diamidino-2-phenylindole in an antifade solution.

(e) The slides are incubated with a Gd-containing cofluorescence solution of EXAMPLE I.

3. Microscopic Analysis (a) The cells are prepared for microscopic analysis by the procedures of EXAMPLE XX i and j and visualized and analyzed by the procedure of EXAMPLE XX k.

(b) Hybridization quality is evaluated by the signal strength, the smoothness of the signal distribution along the chromosome, the lack of accentuated banding, the efficient blocking of the centromeres, and the absence of artifactual ratio variations. Hybridizations in which a concurrent gain of chromosomes I p, 19, and 22 is present are considered artifact prone and are not included in the analysis.

The procedures for preparing and hybridizing DNA in EXAMPLE XX and EXAMPLE XXII can also be applied to fluorescence in situ hybridization and chromosome painting. The EuMac and SmMac labels can be simultaneously excited with DAPI and thus can replace two of the five fluorophores employed by U.S. Pat. No. 6,007,994 (1999) included by reference to combinatorially labeled oligonucleotide probes. These labeled oligonucleotide probes provide sufficient combinations to permit the visualization and simultaneous identification of all 22 autosomal human chromosomes and the human X and Y chromosomes, or defined sub-regions thereof. Such specific labeling of entire chromosomes or defined sub-regions thereof is referred to as "painting." These nucleic acid probes can also be employed for combinatorial labeling of bacteria, viruses and/or lower eukaryotes that may be present in a clinical or non-clinical preparation. Ward et al. (1999) is included by reference. Chapter 8 of Hemmila et al. (1994) which describes the use of other rare-earth complexes for similar purposes is also included by reference.

The procedure described in this example has the advantage of simplifying the instrumentation by requiring one excitation system and a single dichroic mirror for three measurements, the narrow bandwidths of the emissions from both lanthanides minimizes spectral overlap with each other and the DNA stain DAPI as well as with other fluorophores. This simplification will result in both less costly instrumentation and improved accuracy in the quantitation of the DNA probes.

EXAMPLE XXIII

Enhancement of the Luminescence of the TbMac Complex by Gadolinium(III) in Aqueous Micellar Solutions.

A. Materials.

(a) 5.5-dimethyl-1,1,1-trifluoro-2,4-hexanedione (pivaloyltrifluoroacetone), commercially available from Lancaster Synthesis Inc., Catalog No. 1543, $1.00\times10^{-2}$ M stock solution in ethanol.

(b) [Tb-macrocycle(acetate)$_2$](acetate), prepared as previously by De Cola et al. Inorganic Chemistry Vol. 25, 1729–1732 (1986), $1.00\times10^{-3}$ M solution in ethanol. This solution served as primary stock from which more dilute stock solutions were made as necessary.

All other materials were the same as those listed in EXAMPLE I.

B. Procedure

The effect of Gd(III) on the luminescence intensity of the TbMac triacetate complex in aqueous micellar (cofluorescence) solutions was investigated in a series of experiments that utilized the materials listed in EXAMPLE I and followed the protocol described in that Example, with the substitution of TbMac for EuMac and the inclusion of 1,1,1-trimethyl-5,5,5-trifluoro-2,4-pentanedione (pivaloyltrifluoroacetone, HPTFA) among the diketones. The optimum luminescence intensity was observed when the solution contained HPTFA ($8\times10^{-4}$ M) as the diketone, in conjunction with the other components listed in Table 1, each at the concentration shown in that Table.

Optimized cofluorescence solutions containing different concentrations of TbMac ($1.0\times10^{-4}$ M, $1.0\times10^{-5}$ M, $1.0\times10^{-6}$ M) were prepared, and their emission spectra were obtained as described in EXAMPLE I, using a SPEX 1692T spectrofluorometer. For comparison, a solution of TbMac ($1.0\times10^{-4}$ M) in ethanol containing only HPTFA ($4.0\times10^{-4}$ M) was also prepared and examined under the same conditions.

Figure 13:
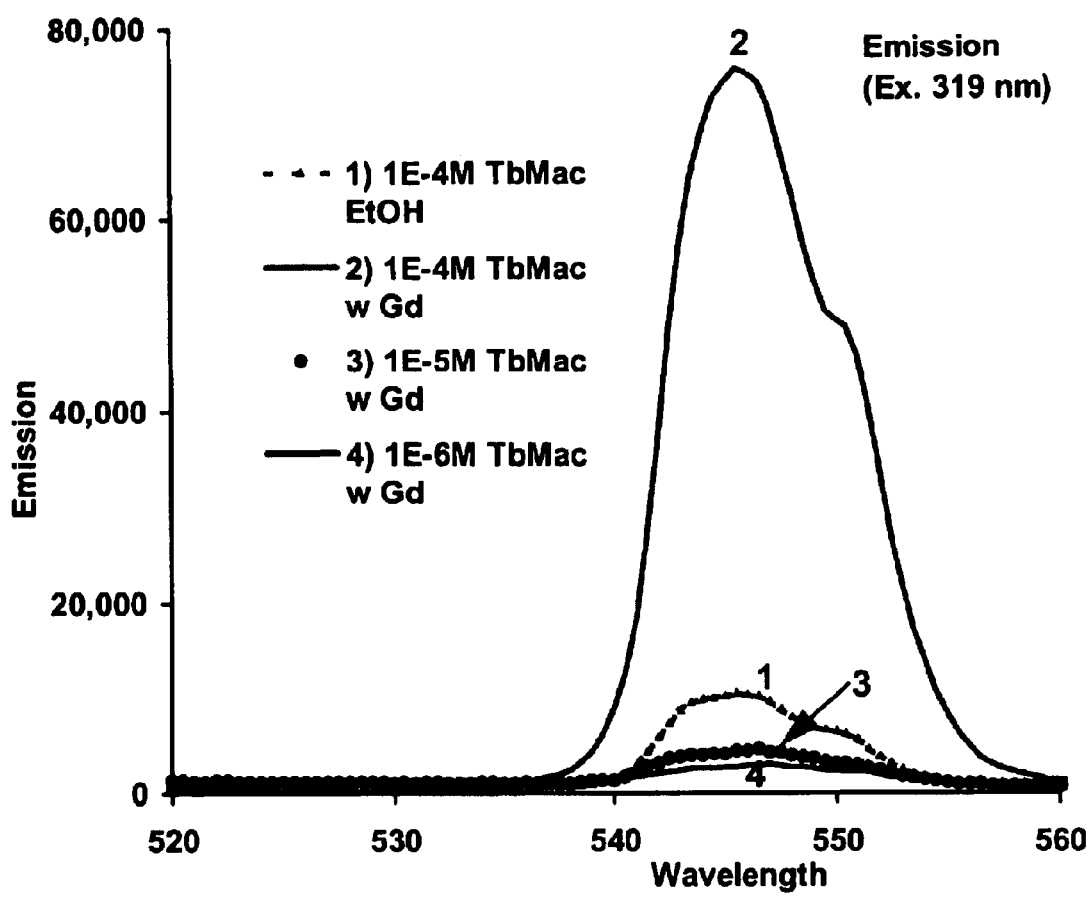
FIG. 13 is a graphical presentation of four emission spectra in the range from 520 to 560 nm.

FIG. 13 shows an emission spectra (excitation, 319 nm) of: (1) an ethanol solution of TbMac, $1.0\times10^{-4}$ M with only HPTFA ($8\times10^{-4}$ M), (2) (3) and (4) Gd-containing cofluorescence-optimized solutions of TbMac, $1.0\times10^{-4}$ M, $1.0\times10^{-5}$ M, $1.0\times10^{-6}$ M, respectively. FIG. 13 illustrates that the luminescence of TbMac is greatly enhanced by the presence of Gd(III) in an aqueous micellar system.

EXAMPLE XXIV

Coupling of the Hexa-aza-macrocyclic Complex of Terbium(III) Acetate Having Pendant (4-isothiocyanatophenyl)methyl Group to an Antibody Via Thiourea Linkages A. Materials (a) A terbium(III) macrocyclic complex having a pendant isothiocyanate group, TbMac-mono-NCS, is prepared as previously described for the europium analog in the procedures of U.S. Pat. No. 5,696,240 Example XXXVI B Step 1 with the substitution of terbium for europium.

(b) PRB-1, an antibody specific for 5BrdU marker for DNA, available from Phoenix Flow Systems, San Diego, Calif.

All other materials are the same as those listed in U.S. Pat. No. 5,696,240 Example XXIX B. Procedure The TbMac-mono-NCS is complex is coupled to PRB-1 anti5BrdU by the procedures of U.S. Pat. No. 5,696,240 Example XXIX with the substitution of the TbMac-mono-NCS for the EuMac-di-NCS and PRB-1 for avidin.

What is claimed is:

1. A method for analysis of a sample containing or suspected of containing at least one analyte, frequently a biologically active compound, said method comprising:
   a) contacting said sample with a functionalized complex of a metal M, where M is a metal ion selected from the group consisting of a lanthanide having atomic number 57–71, an actinide having atomic number 89–103 and yttrium(III) having atomic number 39;
   in a reaction medium under binding conditions, whereby said analyte when present either interacts with said complex to form a conjugate or competes for interaction with a binding material specific for interaction with said complex and with said analyte;
   b) adding to said reaction medium a luminescence-enhancing amount of at least one energy transfer donor compound of yttrium or a 3-valent lanthanide element having atomic number 59–71, provided that the lanthanide element of said functionalized complex and a lanthanide element of said energy transfer donor compound are not identical,
   c) subjecting said reaction medium to excitation energy in the range of 200–400 nm, whereby enhanced luminescence in the range of 500–950 nm is generated,
   d) monitoring said luminescence of the reaction medium to measure in said sample at least one of the following:
      (1) presence and/or concentration of said conjugate;
      (2) presence and/or concentration of the product of the interaction of said complex with said binding material; and
      (3) presence and/or concentration of the product of the interaction of the conjugate with the binding material.

2. The method of claim 1 wherein said functionalized complex forms a compound having the formula

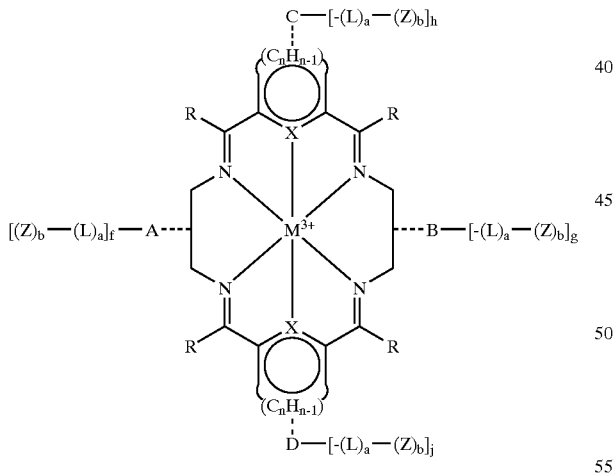

in which from one to two of A, B, C, and D are functionalized groups; L is a bridging/linking moiety between the functionalized macrocycle and a biologically active compound, Z is a residue of a biologically active compound linked to a functionalized group at A, B, C, or D directly or through L, a is zero or one, b is one, and each of f, g, h, and j is independently zero or one, provided that the sum of f, g, h, and j is either one or two.

3. The method of claim 1 in which the analyte is a hapten having a molecular weight in the range of 125–2000 daltons.

4. The method of claim 3 in which the hapten is selected from the group consisting of
   (a) Vitamins, vitamin precursors, and vitamin metabolites including retinol, vitamin K, cobalamin, biotin, folate;
   (b) Hormones and related compounds including
      (i) steroid hormones including estrogen, corticosterone, testosterone, ecdysone,
      (ii) aminoacid derived hormones including thyroxine, epinephrine,
      (iii) prostaglandins,
      (iv) peptide hormones including oxytocin, somatostatin,
   (c) pharmaceuticals including aspirin, penicillin, hydrochlorothiazide,
   (d) Nucleic acid constituents including
      (i) natural and synthetic nucleic acid bases including cytosine, thymine, adenine, guanine, uracil, derivatives of said bases including 5-bromouracil,
      (ii) natural and synthetic nucleosides and deoxynucleosides including 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine,
      (iii) natural and synthetic nucleotides including the mono, di, and triphosphates of 2-deoxyadenosine, 2-deoxycytidine, 2-deoxythymidine, 2-deoxyguanosine, 5-bromo-2-deoxyuridine, adenosine, cytidine, uridine, guanosine, 5-bromouridine,
   (e) drugs of abuse including cocaine, tetrahydrocannabinol,
   (f) histological stains including fluorescein, DAPI
   (g) pesticides including digitoxin,
   (h) and miscellaneous haptens including diphenylhydantoin, quinidine, RDX.

5. The method of claim 1 in which the analyte has a molecular weight greater than 2000 daltons.

6. The method of claim 5 in which the analyte is selected from the group consisting of polyaminoacids, polypeptides, proteins, polysaccharides, nucleic acids, glycosaminoglycans, glycoproteins, ribosomes and
   (a) proteins and their combinations including
      (i) albumins, globulins, hemoglobin, staphylococcal protein A, alpha-fetoprotein, retinol-binding protein, avidin, streptavidin, C-reactive protein, collagen, keratin,
      (ii) immunoglobulins including IgG, IgM, IgA, IgE,
      (iii) Hormones including lymphokines, follicle stimulating hormone, and thyroid stimulating hormone,
      (iv) enzymes including trypsin, pepsin, reverse transcriptases
      (v) cell surface antigens on T- and B-lymphocytes, i.e. CD-4, CD-8, CD-20 proteins, and the leukocyte cell surface antigens, such as described in the presently employed CD nomenclature;
      (vi) blood group antigens including A, B and Rh,
      (vii) major histocompatibility antigens both of class 1 and class 2,
      (viii) hormone receptors including estrogen receptor, progesterone receptor, and glucocorticoid receptor,
      (ix) cell cycle associated proteins including protein kinases, cyclins, PCNA, p53,
      (x) antigens associated with cancer diagnosis and therapy including BRCA(s) carcinoembryonic antigen, HPV 16, HPV 18, MDR, c-neu; tumor suppressor proteins, p53 and retinalblastoma,
      (xi) apoptosis related markers including annexin V, bak, bcl-2, fas caspases, nuclear matrix protein, cytochrome c, nucleosome, (xii) toxins including cholera toxin, diphtheria toxin, and botulinum toxin, snake venom toxins, tetrodotoxin, saxitoxin, (xiii) lectins including concanavalin, wheat germ agglutinin, soy bean agglutinin, (b) polysialic acids including chitin;

(c) polynucleotides including
  (i) RNAs including segments of the HIV genome, human hemoglobin A messenger RNA,
  (ii) DNAs including chromosome specific sequences, centromeres, telomere specific sequences, single copy sequences from normal tissues, single copy sequences from tumors.

7. The method of claim 1 in which said luminescence is monitored with time-gated fluorescence instrumentation.

8. The method of claim 1 in which said luminescence is monitored with fluorescence instrumentation that is equipped with a continuous light source.

9. The method of claim 1 in which said luminescence is monitored with fluorescence instrumentation which measures multiple samples that are each automatically positioned in the luminescence detection zone.

10. The method of claim 1 in which said luminescence is monitored with fluorescence instrumentation which permits the imaging of the analyte.

11. The method of claim 10 in which said fluorescence instrumentation permits the measurement of the analyte at various points in the image.

12. The method of claim 11 in which said fluorescence instrumentation measures, records, processes, and/or displays the spatial distribution of one or more analytes.

13. The method of claim 12 in which said fluorescence instrumentation is a digital fluorescence microscope.

14. The method of claim 12 in which said fluorescence instrumentation is employed for comparative genomic hybridization.

15. The method of claim 12 in which said fluorescence instrumentation measures the analytes on a microarray.

16. The method of claim 1 in which the luminescence of an analyte in a nonaqueous environment is monitored and measured.

17. The method of claim 1 in which the analyte is monitored and measured in the dry state.

18. A spectrophotometrically detectable luminescent composition comprising water, a micelle-producing amount of at least one surfactant, at least $1 \times 10^{-10}$ moles/liter of at least one energy transfer acceptor lanthanide element functionalized complex having an emission spectrum peak in the range from 500 to 950 nanometers, and a luminescence-enhancing amount of at least one energy transfer donor compound of yttrium or a 3-valent lanthanide element having atomic number 59–71, provided that the lanthanide element of said functionalized complex and the lanthanide element of said energy transfer donor compound are not identical.

19. The composition of claim 18, wherein said energy acceptor lanthanide element functionalized complex is a macrocycle.

20. The composition of claim 19, wherein said macrocycle contains at least nine ring atoms of which at least three are donor atoms.

21. A composition according to claim 19, in which the lanthanide macrocycle has eighteen ring members.

22. A composition according to claim 18 which is a cloudy solution.

23. The composition resulting from the transfer of a composition of claim 18 to a non-aqueous environment.

24. The composition resulting from the transfer of a composition of claim 18 to a non-aqueous environment and removal of water.

* * * * *